(12) United States Patent
Kuhns et al.

(10) Patent No.: US 6,551,333 B2
(45) Date of Patent: Apr. 22, 2003

(54) METHOD FOR ATTACHING HERNIA MESH

(75) Inventors: Jesse J. Kuhns, Cincinnati, OH (US); Robert L. Koch, Cincinnati, OH (US); Bennie Thompson, Blue Ash, OH (US); Richard P. Fuchs, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 10/016,419

(22) Filed: Dec. 10, 2001

(65) Prior Publication Data

US 2002/0087170 A1 Jul. 4, 2002

Related U.S. Application Data

(63) Continuation-in-part of application No. 09/692,633, filed on Oct. 19, 2000, and a continuation-in-part of application No. 09/692,627, filed on Oct. 19, 2000, and a continuation-in-part of application No. 09/692,636, filed on Oct. 19, 2000.

(51) Int. Cl.[7] .............................................. A61B 17/08
(52) U.S. Cl. ........................ 606/151; 606/139; 606/220; 606/78; 606/218
(58) Field of Search ................................ 606/220, 232, 606/72, 139, 144, 75, 78, 59, 145, 151, 219, 1, 158, 157, 76, 218

(56) References Cited

U.S. PATENT DOCUMENTS

| | | |
|---|---|---|
| 3,740,994 A | 6/1973 | De Carlo, Jr. |
| 4,325,376 A | 4/1982 | Klieman et al. |
| 4,471,780 A | 9/1984 | Menges et al. |
| 4,478,220 A | 10/1984 | Di Giovanni et al. |
| 4,527,724 A | 7/1985 | Chow et al. |
| 4,665,906 A | 5/1987 | Jervis |
| 4,925,445 A | 5/1990 | Sakamoto et al. |
| 5,171,249 A | 12/1992 | Stefanchik et al. |
| 5,203,864 A | 4/1993 | Phillips |
| 5,217,486 A | 6/1993 | Rice et al. |
| 5,290,297 A | 3/1994 | Phillips |
| 5,470,010 A | 11/1995 | Rothfuss et al. |
| 5,582,616 A | 12/1996 | Bolduc et al. |
| 5,601,573 A | 2/1997 | Folgelberg et al. |
| 5,673,842 A | 10/1997 | Bittner et al. |
| 5,810,882 A | 9/1998 | Bolduc et al. |
| 5,830,221 A | 11/1998 | Stein et al. |
| 5,833,700 A | 11/1998 | Folgelberg et al. |
| 5,878,938 A | 3/1999 | Bittner et al. |
| 5,921,997 A | 7/1999 | Fogelberg et al. |
| 6,113,611 A | 9/2000 | Allen et al. |

FOREIGN PATENT DOCUMENTS

| | | |
|---|---|---|
| EP | 0392750 B1 | 1/1995 |
| WO | 98/11814 A1 | 3/1998 |

*Primary Examiner*—A Vanatta
*Assistant Examiner*—Robert H. Muromoto
(74) *Attorney, Agent, or Firm*—Dean Garner

(57) ABSTRACT

A method for delivering a plurality of individual surgical fasteners. The method includes the step of providing a surgical fastener delivery device having a drive mechanism with distal and proximal ends, the drive mechanism comprising moving and fixed opposing members, the moving member being moveable proximally and distally with respect to the delivery device, and the fixed member being fixed with respect to the delivery device, the device having the plurality of surgical fasteners located between the moving and the fixed members. The method further involves the step of penetrating tissue and placing a distal end one of the surgical fasteners within tissue, by moving the moving member distally. The method further involves the step of deploying a distal end of one of the surgical fasteners by moving the moving member proximally.

6 Claims, 28 Drawing Sheets

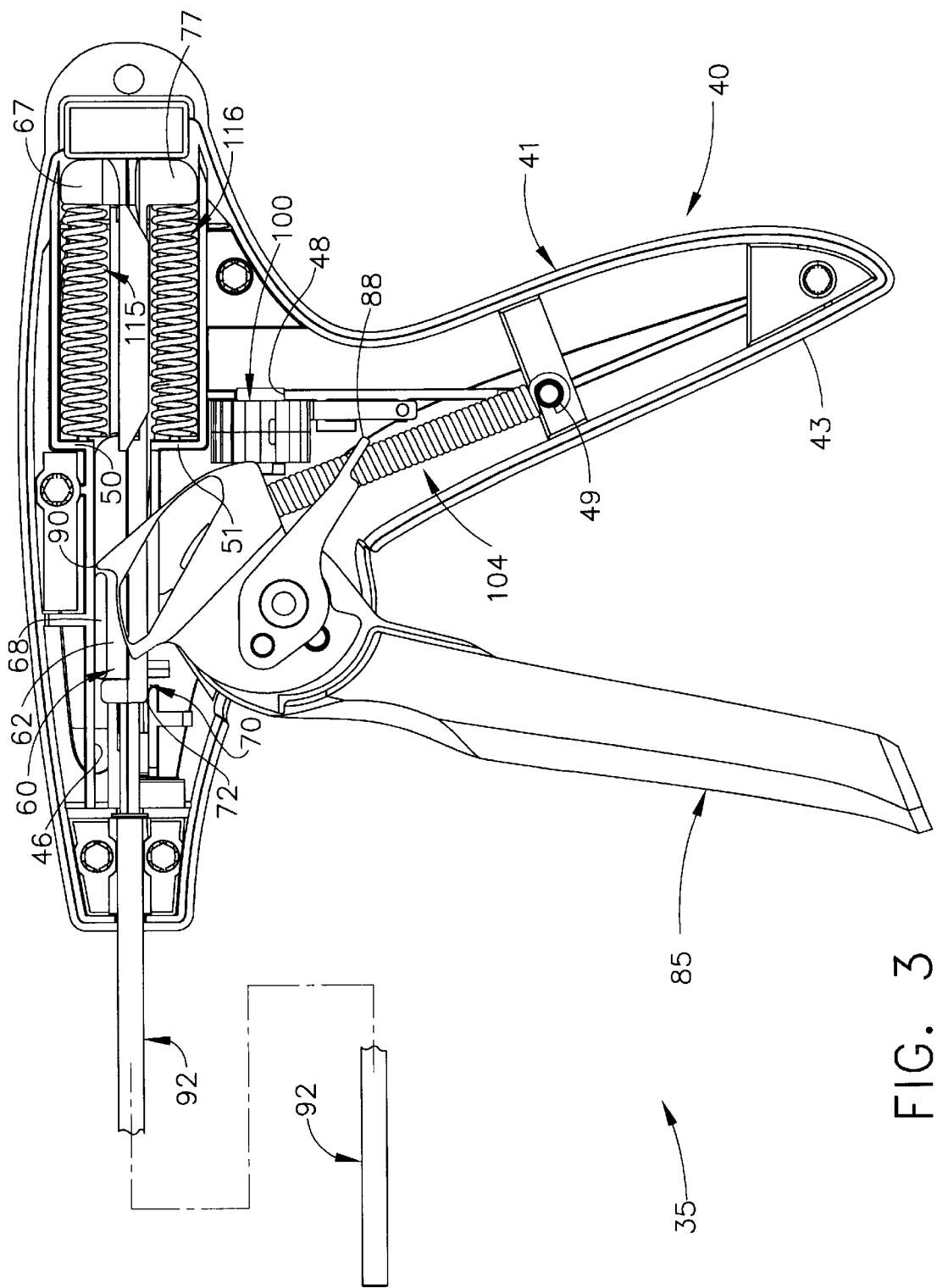

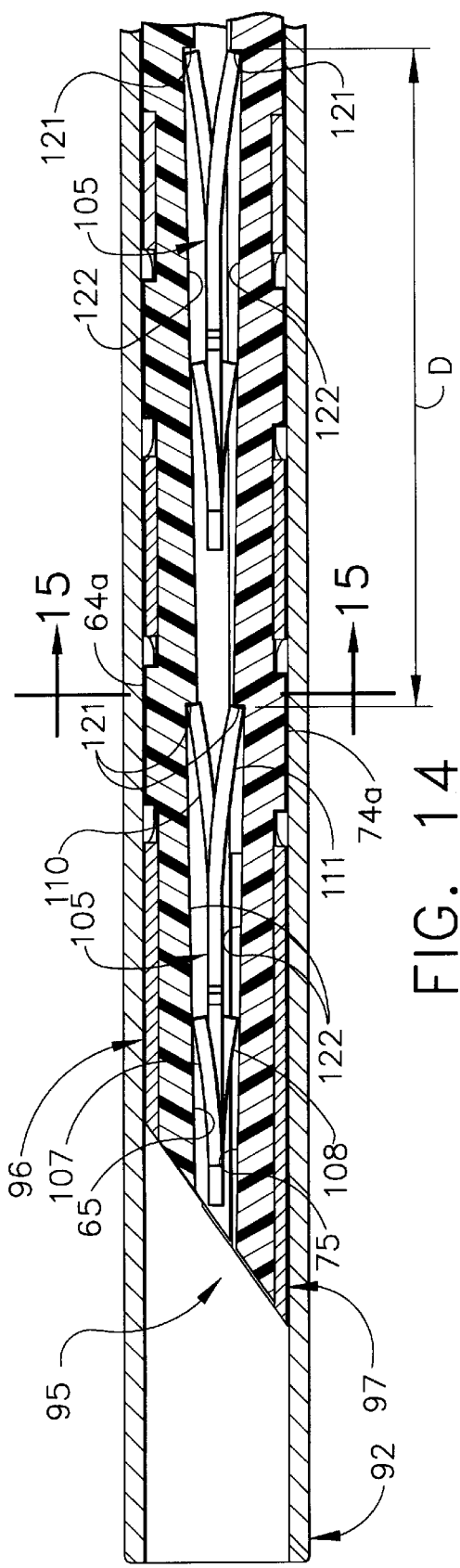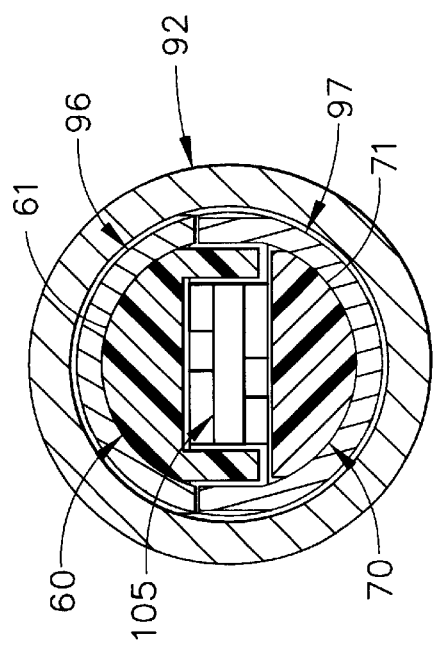
FIG. 14
FIG. 15

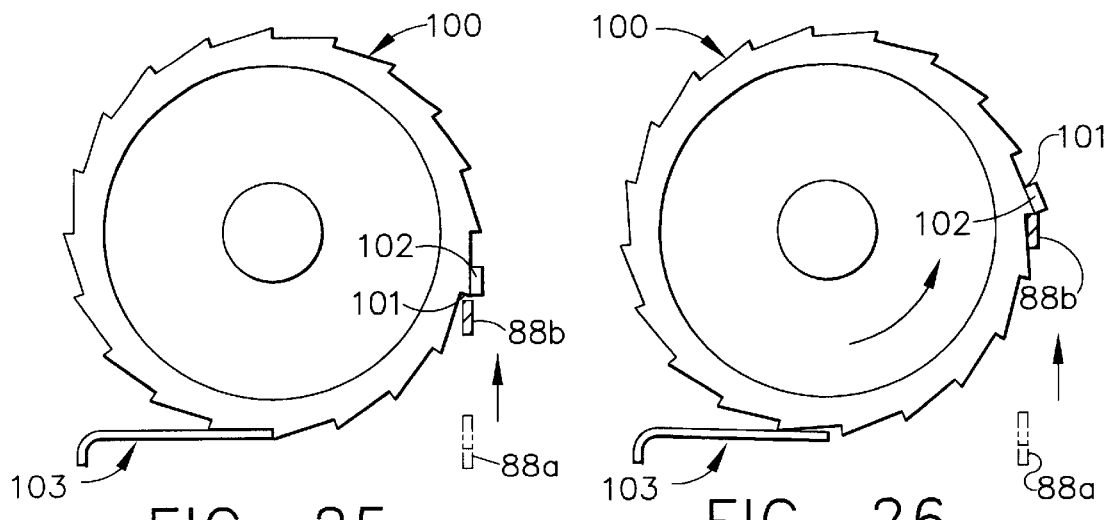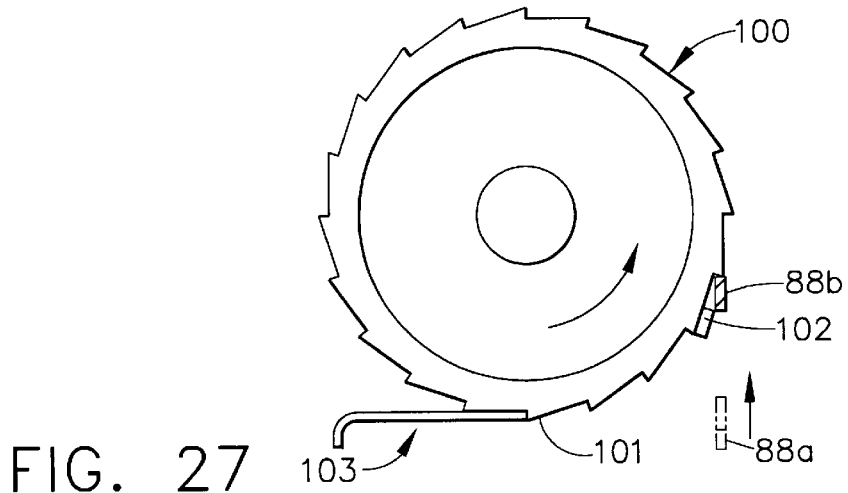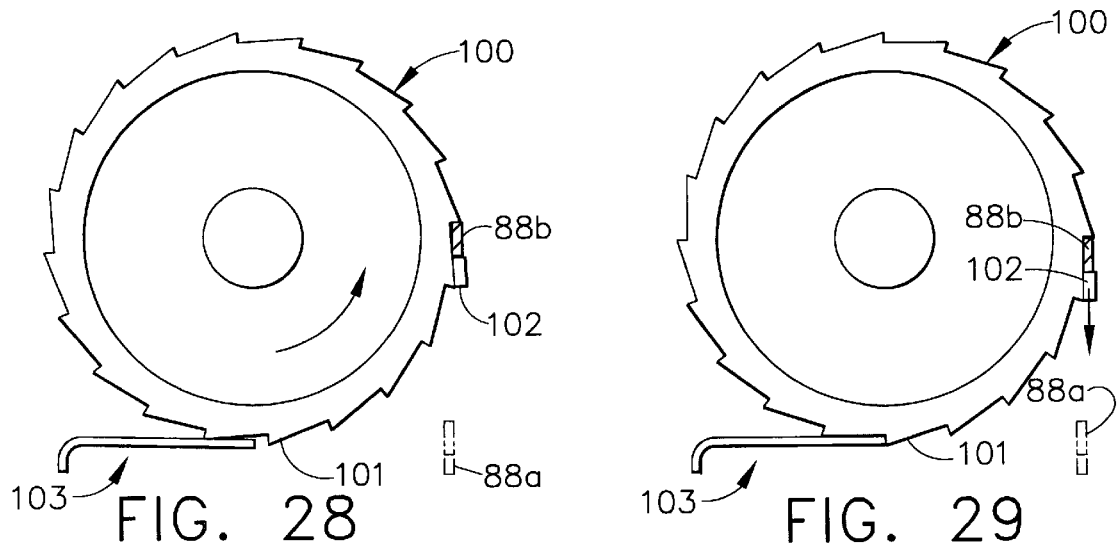

METHOD FOR ATTACHING HERNIA MESH

This Continuation in Part application is related to the following copending patent applications: application Ser. No. 09/692,633; application Ser. No. 09/692,627 and application Ser. No. 09/692,636 Filed Oct. 19, 2002, which are hereby incorporated herein by reference.

FIELD OF THE INVENTION

The present invention relates, in general, to the repair of defects in tissue and includes a novel surgical method for placing a surgical element into tissue with a surgical instrument. More particularly, to the method of use of the surgical fastening instrument and surgical fastener in combination with a prosthetic for the repair of an inguinal hernia.

BACKGROUND OF THE INVENTION

An inguinal hernia is a condition where a small loop of bowel or intestine protrudes through a weak place or defect within the lower abdominal muscle wall or groin of a patient. This condition commonly occurs in humans, particularly males. Hernias of this type can be a congenital defect wherein the patient is born with this problem, or can be caused by straining or lifting heavy objects. Heavy lifting may be known to create a large amount of stress upon the abdominal wall and can cause a rupture or tearing at a weak point of the abdominal muscle to create the defect or opening. In any case, the patient can be left with an unsightly bulge of intestinal tissue protruding through the defect, pain, reduced lifting abilities, and in some cases, impaction of the bowel, or possibly other complications if the flow of blood is cut off to the protruding tissue.

A common solution to this problem can be surgery. In the surgical procedure, the defect is accessed and carefully examined, either through an open incision or endoscopically through an access port such as a trocar. In either case, the careful examination can be well appreciated, as a network of vessels and nerves exist in the area of a typical defect, which requires a surgeon to conduct a hernia repair with great skill and caution. Within this area can be found vascular structures such as gastric vessels, the external iliac vessels, and the inferior epigastric vessels, and reproductive vessels such as the vas deferens extending through the inguinal floor.

Once the surgeon is familiar with the anatomy of a patient, the surgeon carefully pushes the bowel back into the patient's abdomen through the defect. Repairing the defect can involve closure of the defect with sutures or fasteners but generally involves placing a surgical prosthetic such as a mesh patch over the open defect, and attaching the mesh patch to the inguinal floor with conventional suture or with surgical fasteners. The mesh patch acts as a barrier and prevents expulsion of bowel through the defect. Suturing of the mesh patch to the inguinal floor can be well suited to open procedures but can be much more difficult and time consuming with endoscopic procedures. With the adoption of endoscopic surgery, endoscopic surgical instruments that apply surgical fasteners can be used. However, the tissue of the inguinal floor may offer special challenges to the surgeon when a needle or fastener is used to penetrate structures such as Cooper's ligament.

At present, there are a variety of surgical instruments and fasteners available for the surgeon to use in an endoscopic or open procedure to attach the mesh patch to the inguinal floor. One of the earliest types of endoscopic surgical instruments used is a surgical stapler. A plurality or stack of these unformed staples may be generally contained within a stapling cartridge in a serial fashion, and may be sequentially advanced or fed within the instrument by a spring mechanism. A secondary valving or feeding mechanism may be employed to separate the distal most staple from the stack, to hold the remainder of the spring loaded stack, and may be used to feed the distal most stapler into the staple forming mechanism. Feeding mechanisms of this type are found in U.S. Pat. Nos. 5,470,010 and 5,582,616, also by Robert Rothfuss et al.

Another hernia mesh attachment instrument uses a helical wire fastener that resembles a small section of spring. Multiple helical wire fasteners may be stored serially within the 5 mm shaft, and may be corkscrewed or rotated into tissue. A load spring may be used to bias or feed the plurality of helical fasteners distally within the shaft. A protrusion extends into the shaft to possibly prevent the ejection of the stack of fasteners by the load spring and may permit passage of a rotating fastener. Instruments and fasteners of these types are found in U.S. Pat. Nos. 5,582,616 5,810,882 by Lee Bolduc et al., and in U.S. Pat. No. 5,830,221 by Jeffrey Stein et al.

Whereas the above surgical instruments may be used for hernia fastening applications, they use a spring mechanism to feed a plurality of fasteners through the surgical instrument. Spring mechanisms typically use a long soft coil spring to push a stack of fasteners through a guide or track within the shaft of the surgical instrument. These types of feeding mechanisms may be generally simple and reliable, but may require an additional secondary valving mechanism or protrusion to separate and feed one fastener from the stack.

Other surgical fasteners may be used for hernia mesh attachment but utilize either a reloadable single shot instrument or a rotary magazine that holds a small number of fasteners. These types of surgical fastening instruments can be found in U.S. Pat. Nos. 5,203,864 and 5,290,297, both by Edward Phillips. These instruments have not gained acceptance by the surgical community, possibly due to their single shot capabilities and the large size of the rotary magazine, which can restrict such an instrument to an open procedure.

Whereas all the above surgical instruments may be used for hernia fastening applications, they either use a spring mechanism to feed the plurality of fasteners through the surgical instrument, or a rotary magazine in lieu of a feeding mechanism. Other types of surgical fasteners may be available, such as surgical clips, and they can utilize feeding mechanisms that do not require the use of a spring to feed the clips distally. A reciprocating feeding mechanism is described in U.S. Pat. Nos., 5,601,573, 5,833,700, and 5,921,997 by Fogelberg et al. Fogelberg et al. teaches a clip applier with a feeding mechanism that utilizes a reciprocating feed bar to feed a serial stack of clips. A feeder shoe may operably engage with and move with the distally moving feed bar and may slidingly engages with the proximally moving feed bar. Thus, the feeder shoe may index or push the stack of clips distally with the distally moving feed bar and remains stationary relative to the proximally moving feed bar. A valving mechanism may be also required to separate the distal most clip from the stack and to hold the stack stationary as the distal most clip may be applied onto a vessel. Whereas Fogelberg et al. teaches a reciprocating feeding mechanism with a single reciprocating member, he does not teach the use of the clip applier in the attachment of hernia mesh, nor does he teach the individual driving or feeding of each clip by a moving member.

Another fastener feeding mechanism that uses reciprocation is that disclosed in U.S. Pat. No. 4,325,376 by Klieman et al. A clip applier that stores a plurality of clips in a serial fashion within a clip magazine is disclosed. The clips are in a stack wherein the proximal most clip may be pushed or fed distally by a pawl that may be ratcheted or indexed distally by a reciprocating member or ratchet blade with each actuation of the instrument. As the pawl indexes distally, it can push the stack of clips distally. A secondary valving mechanism may be also described. Thus, the feeding mechanism of Klieman et al. teaches the use a single reciprocating member and pawl to push or feed the stack of clips distally, and may requires a secondary valving mechanism to feed the distal most clip.

U.S. Pat. No. 3,740,994 by DeCarlo Jr. describes a novel reciprocating feeding mechanism that may index a plurality of staples or clips, and may ready them for discharge by reciprocating one of a pair of opposing leaf spring assemblies. The staples reside serially within a guide rail with a fixed leaf spring assembly extending into the plane of the guide rail. A reciprocating leaf spring assembly may opposedly extend inwardly towards the fixed leaf spring assembly. As the a reciprocating leaf spring assembly moves distally, each of individual leaf springs of the assembly may engage a staple and move it distally. The distally moving plurality of staples deflect the local individual leaf springs of the fixed leaf spring assembly, and the deflected leaf springs may return to the un-deflected position after passage of the staple. As the moving leaf spring assembly moves proximally, the leaf springs of the fixed leaf spring assembly hold the staples stationary and prevent distal movement thereof. A secondary guide rail and valving mechanism may be provided to separate a single staple from the stack for forming and can hold the stack of staples stationary as the single clip is formed.

Additionally, similar feeding mechanisms are disclosed in U.S. Pat. No. 4,478,220 by Di Giovanni et al. and U.S. Pat. No. 4,471,780 by Menges et al. Both of these related patents teach a reciprocating feeding mechanism that uses one fixed member and one reciprocating member to feed or index a plurality of clips distally. Angled flexible fingers may be hingedly attached to the reciprocating member and operatively engage the clips when moving distally, and slidingly engage with the clips when moving proximally. The angled flexible fingers within the fixed member deflect out of the way when the clips move distally and spring up to stop proximal movement of the clip after the clip has passed. A secondary valving mechanism is also disclosed.

Thus, the feeding mechanism of DeCarlo et al., Di Giovanni et al., and Menges et al. operatively engage and individually move each clip distally between a single reciprocating member and a fixed member. However each instrument may require a secondary valving mechanism for the feeding and forming of the distal most clip.

The majority of the feeding mechanisms described above can require two feeding mechanisms; a primary feeding mechanism to feed a plurality of clips distally, and a secondary valving or feeding mechanism to separate and feed the distal most fastener while preventing the distal movement of the remaining fasteners. Such additional mechanisms may be costly and increase the size or diameter of the instrument size. Likewise, the single shot or rotary magazines may have limitations. What may be needed is an improved reciprocating feeding mechanism that may not require the use of a secondary valving mechanism, and may simultaneously engage with and independently drive each fastener distally. Such a mechanism can have two reciprocating members and could provide superior advantages such as lower cost, reduced complexity, and a smaller diameter shaft.

SUMMARY OF THE INVENTION

In accordance with the present invention, there is provided a method for delivering a plurality of individual surgical fasteners. The method includes the step of providing a surgical fastener delivery device having a drive mechanism with distal and proximal ends, the drive mechanism comprising moving and fixed opposing members, the moving member being moveable proximally and distally with respect to the delivery device, and the fixed member being fixed with respect to the delivery device, the device having the plurality of surgical fasteners located between the moving and the fixed members. The method further involves the step of penetrating tissue and placing a distal end one of the surgical fasteners within tissue, by moving the moving member distally. The method further involves the step of deploying a distal end of one of the surgical fasteners by moving the moving member proximally.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 3 is a side view, in cross section, of a first side of the surgical instrument of FIG. 1 with the left handle half removed, wherein all of the internal elements are shown assembled and the trigger is in an open position;

FIG. 14 is a cross-sectional side view of a distal end of a shaft of the surgical instrument fastener of the present invention showing the end effector normally retracted therein and a plurality of surgical fasteners of the present invention contained therein;

FIG. 15 is a cross-sectional view 10—10 of the shaft and the end effector of FIG. 9 and showing a passageway and a fastener of the present invention contained therein;

FIG. 25 is a fragmentary cross-section view of the lockout mechanism of the present invention showing the lockout wheel in an initial position and engaged with a wheel detent, wherein the lockout arm is moving upwardly from a start position (dashed lines) to a second position (cross section) adjacent to the lockout wheel;

FIG. 26 is a fragmentary cross-section view of FIG. 25 showing the upwardly moving lockout arm engaging with a first tooth of the lockout wheel, wherein the engagement has rotated the locking wheel one tooth counterclockwise and the locking arm is preparing to return to the initial position (dashed lines);

FIG. 27 is a fragmentary cross-section view of FIG. 26 showing the upwardly moving lockout arm engaging with a final tooth of the lockout wheel, wherein the repeated firing of the trigger has rotated the lockout wheel to the final tooth, and a locking tab is positioned just below the upwardly moving locking arm (cross section);

FIG. 28 is a fragmentary cross-section view of FIG. 27 showing the upwardly moving lockout arm further engaging with a final tooth of the lockout wheel, wherein the lockout wheel has rotated counterclockwise to position the locking tab below the lockout arm;

FIG. 29 is a fragmentary cross-section view of FIG. 28 showing the detent arm preventing further rotation of the locking wheel and the lockout arm attached to the trigger captured between a tooth and the locking arm of the locking wheel.

DETAILED DESCRIPTION OF THE INVENTION

The present invention pertains to a novel surgical method for the repair of tissue defects in a human patient. More particularly, the invention concerns a novel surgical method for using a surgical instrument and a surgical element or fastener to attach a prosthetic in the repair of an inguinal hernia.

By way of example, the present invention is illustrated and described in conjunction with a repair of an inguinal hernia. However, it should be understood that the present invention is applicable to various other surgical procedures that require the repair of defects in tissue.

The Surgical Instrument

Figure 1:
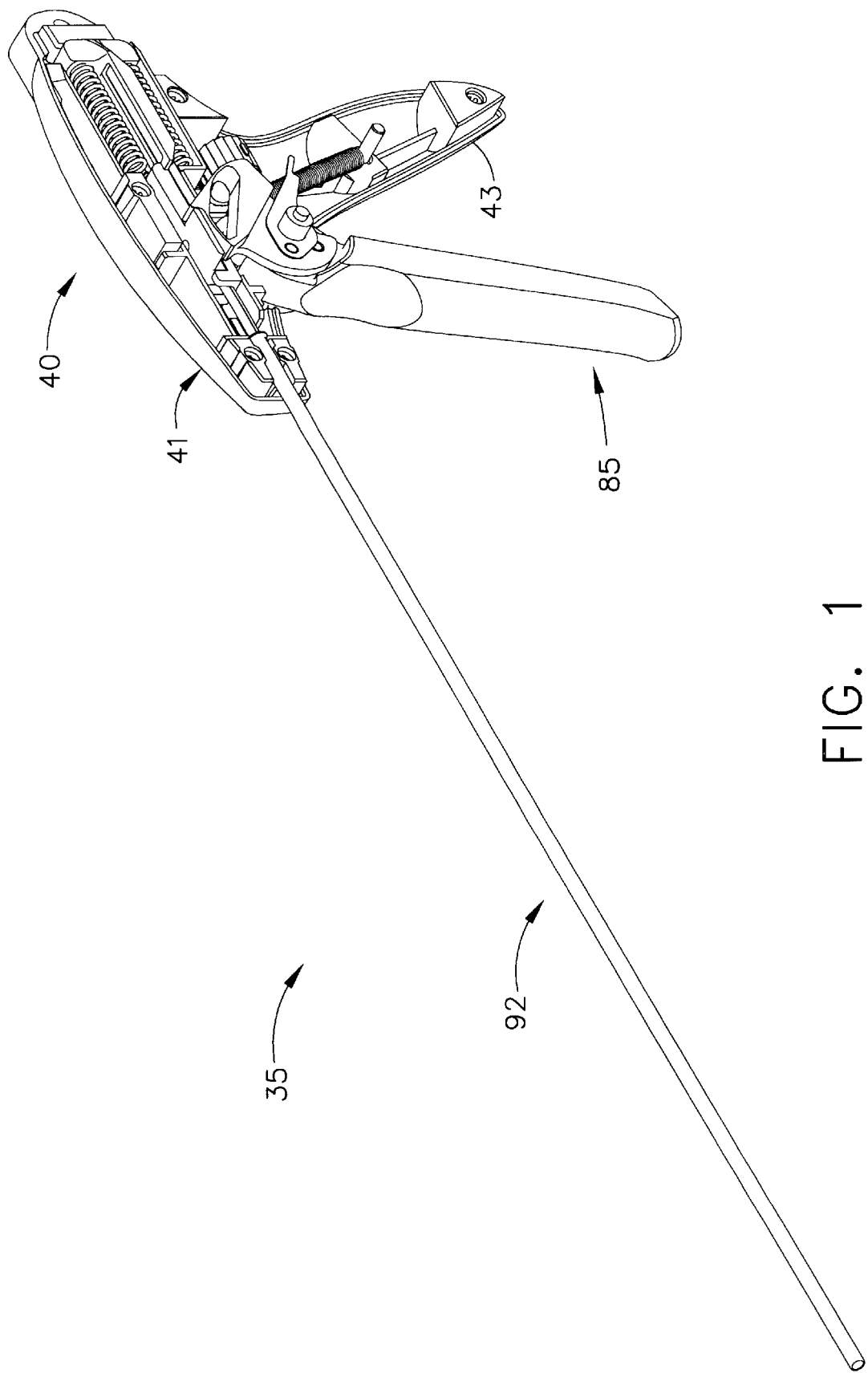
FIG. 1 is an isometric view of a surgical instrument wherein a left handle half is removed to show the elements within when a trigger is in an open position, the surgical instrument having a first and a second slider moveable from a proximal to a distal position.
Figure 2:
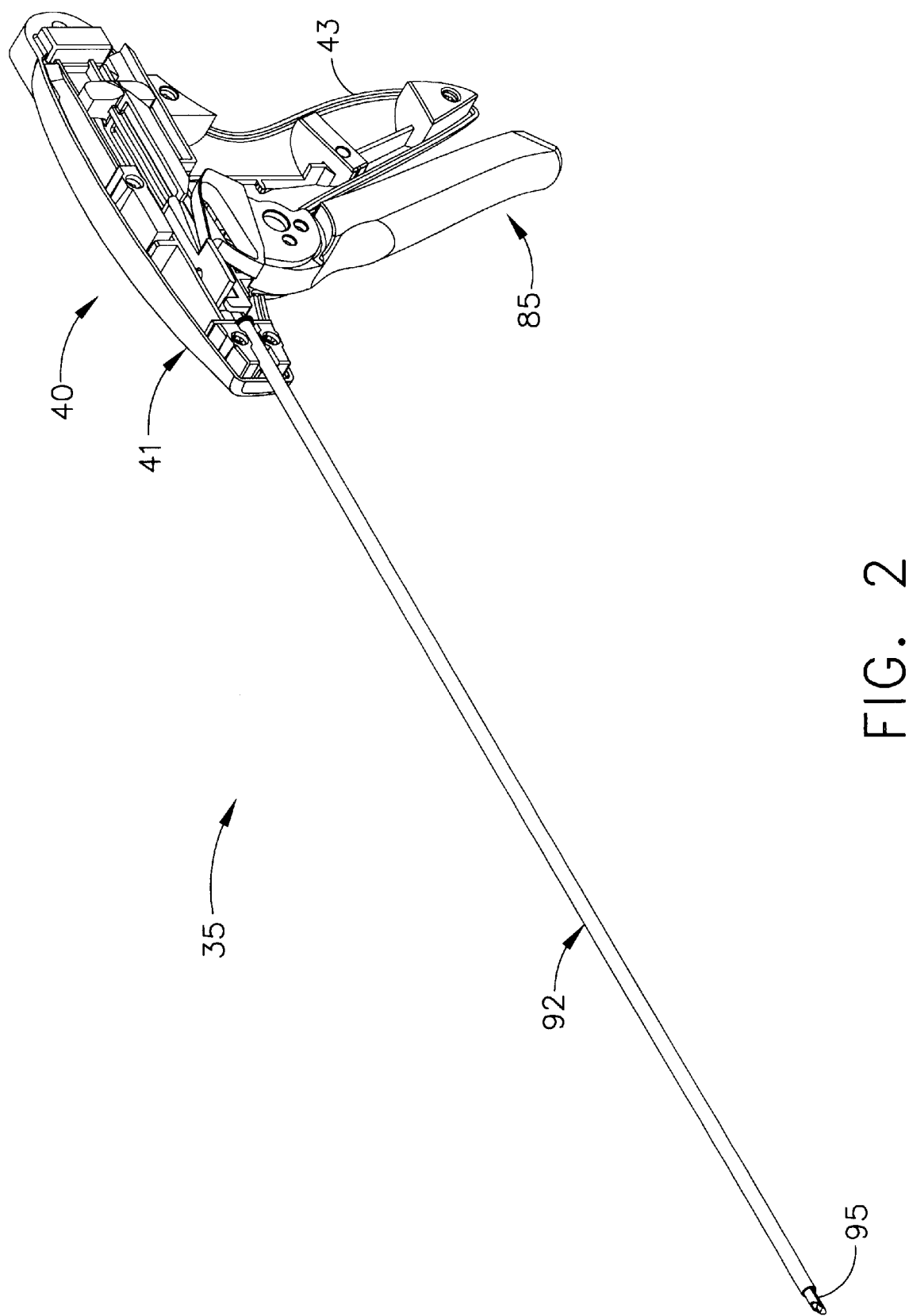
FIG. 2 is an isometric view of the surgical instrument of FIG. 1 wherein the trigger is moved from the open position of FIG. 1 to a closed position as shown to move the first and second sliders to the distal position, and to extend an end effector attached to the first and second sliders from the surgical instrument.

As best shown in FIGS. 1 and 2, the surgical instrument or fastener delivery device of the present invention comprises a hand held surgical instrument 35 containing a plurality of surgical fasteners or surgical elements that can be generally used for the attachment of a prosthetic to tissue, or as a tissue marker. The surgical fasteners 105 of the present invention may be formed from a superelastic nickel titanium alloy, may be stored within the surgical instrument in a compressed or collapsed state, and may expand to an unconstrained state upon release from the surgical instrument. Actuation of the instrument simultaneously releases a fastener 105 of the present invention from a distal end of the instrument and indexes the plurality of fasteners 105 within the instrument.

Surgical instrument 35 of the present invention has a handle 40, an elongated shaft 92 extending distally from the handle 40, and a trigger 85 extending downwardly from the handle 40. Handle 40 has a right half 41 and a left half 42 that may be generally mirror images of each other and, in FIGS. 1 and 2, the left half 42 is omitted. Elongated shaft 92 may be fixedly attached to the handle 40, and can be formed from a rigid hollow material such as stainless steel tubing. A grip 43 can be fixedly attached to and extends downwardly from a proximal end of handle 40 and adjacent to the trigger 85. Trigger 85 pivotably mounts within handle 40 and can be moveable from an open position as shown in FIG. 1 to a closed position adjacent to the grip 43 as shown in FIG. 2. Movement of the trigger 85 to the closed position extends an end effector 95 from a distal end of the shaft 92 (FIG. 2) for the placement and release of a fastener.

Figure 2B:
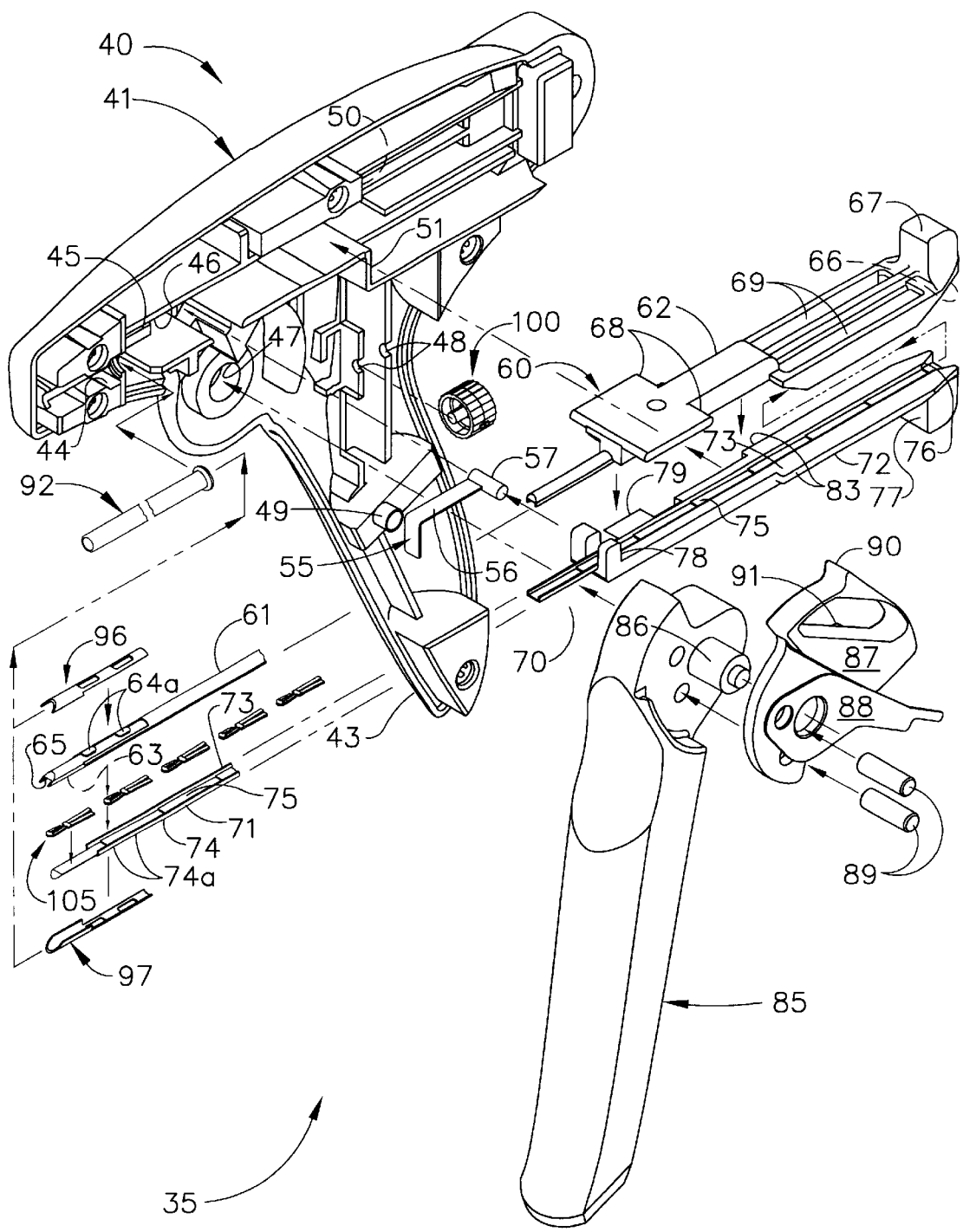
FIG. 2B is an exploded isometric view of some of the internal elements of the surgical instrument of FIG. 1 including the first and second sliders, with some elements removed for clarity.

FIG. 2B is an isometric exploded view of the majority of the elements found within the surgical instrument 35. The exploded view is provided to familiarize the reader with the key elements contained therein, and the method of assembly used to form the surgical instrument 35. For clarity, a number of elements such as the left handle half 42 can be removed. Some of the elements of FIG. 2B may be complex in shape and the reader may be advised to return to this figure for identification or comprehension of features referenced below. The elements of the surgical instrument 35 may be contained within the right and left handle halves 41,42 which can be formed from an engineering thermoplastic such as styrene, polycarbonate, or any one of a number of suitable materials. A shaft slot 44 may be located at the distal end of the upper portion of the handle halves 41,42 for the reception and retention of the shaft 92 therein.

A latch slot 45 may be located proximally to and below the shaft slot 44 within the right handle half 41. Latch slot 45 may be right-angled in shape and may be provided for the reception of a latch 55 therein. Latch 55 can have a rigid latch post 57 at a distal end and a right-angled beam 56 extending distally therefrom. Beam 56 may be formed from a resilient spring material such as stainless steel. A distal end of beam 56 may be captured and held within the latch slot 45 with a significant amount of the beam 56 cantilevering therefrom. The cantilever portion of the beam 56 enables the latch post 57 to move freely up and down as the beam 56 deflects. The significance of the latch 55 will be described later.

A first and a second slider 60, 70 may be opposing members that extend generally proximally and distally throughout the shaft 92 and handle 40 of the surgical instrument 35 and form a drive mechanism for the fasteners 105. First and second sliders 60, 70 may be moveable proximally and distally with respect to the surgical instrument 35 and individually with respect to each other, and may be slidably retained within a pair of guide slots 46 located within each of the handle halves 41, 42. In FIG. 2B, the first and second sliders 60, 70 have a proximal and a distal end and are shown spaced apart prior to assembly to show a plurality of fasteners 105 that may be stored therebetween. Fasteners 105 can extend along the entire length of the first and second sliders 60, 70. First and second sliders 60, 70 can have distal first and second feed members 61, 71 that slidably mount within the shaft 92, and can have a larger proximal first and second sequencing member 62, 72 that slidably mount within the handle halves 41, 42. First and second feed members 61, 71 may be semi-circular in cross section and can have a first and second outer surface 64, 74. A pair of first and second stab posts 64a, 74a can extend outwardly from a distal end of each first and second outer surface 64, 74 respectively. A first and second contact surface 63, 73 can complete the semi-circular cross section of the first and second feed members 61, 71 respectively. First and second contact surfaces 63, 73 can opposably face each other along the entire length of the first and second sliders 60, 70 and can have a first and second fastener channel 65, 75 extending therein. When assembled, first and second sliders 60, 70 can make sliding contact along the entire length of first and second contact surfaces 63, 73 and first and second fastener channels 65, 75 can form a hollow rectangular channel for the holding and feeding of fasteners 105 serially therethrough (FIG. 15).

The fastener channels 65, 75 of the first and second sliders 60, 70 may be "U" shaped for the reception of the fasteners 105 therein and can have a pair of opposed inner surfaces or channel floors for engaging with the fasteners 105. The inner surfaces can have a plurality of projections or fastener drive features spaced thereon for engagement with the fasteners 105. As best shown in the enlarged FIG. 14, these projections or sawteeth 120, can extend proximally to distally along the entire length of the floors of the first and second fastener channels 65, 75 and may be equally spaced a longitudinal distance "D" apart. The distance "D" may be between 8 inches and 0.005 inches. The spacing "D" of the present invention may be 0.475 inches. The spacing "D" can space the fasteners apart from one another so that the fasteners do not engage or touch as they are fed within the surgical instrument 35. Each sawtooth 120 can have a proximal incline 122 and a distal step 121 as shown. The role of the sawteeth 120 in the feeding of the fasteners 105 will be discussed in detail later.

At the distal end of the first and second fastener channels 65, 75 may be a first and a second fastener guide 66, 76 respectively which may be a tapered lead-in at the proximal end of fastener channels 65, 75 and can assist in the loading of the fasteners 105 therein. These fastener guides 66, 76 may be generally mirror images of each other. In FIG. 2B, the first fastener guide 66 is hidden.

The larger proximal portions of the first and second sliders 60, 70 are the first and second sequencing members 62, 72, which may control the timing and sequencing of a fastener feeding mechanism that releases a fastener from the distal end of the instrument, and indexes or feeds the plurality of fasteners distally within the instrument. The first sequencing member 62 can have a pair of guide ribs 68 extending laterally outwardly from either side and a first spring stop 67 extending upwardly at a proximal end. Guide ribs 68 can mount within the guide slots 46 of the right and left handle halves 41, 42 and can slidably secure the assembled sliders 60, 70 within the handle 40. A pair of "C" shaped guide channels 69 may be located underneath and extend longitudinally along the proximal half of the first sequencing member 62. The second sequencing member 72 can have second spring stop 77 located at a proximal end of second sequencing member 72 and a forked stop 78 extending upwardly at a distal end. A cam plate 79 can extend outwardly from the far side of the second sequencing member 72 towards the right handle half 41. A pair of slider ribs 83 can extends laterally outward along the proximal half of the second sequencing member 72. First and second sliders 60, 70 can be formed as a single piece from an engineering thermoplastic such as a liquid crystal polymer, a polycarbonate, nylon, a styrene or the like.

The first and second sliders 60,70 may be slidably interlocked together by inserting the pair of slider ribs 83 located on the second sequencing member 72 into the pair of guide channels 69 of the first sequencing member 62. First and second sliders 60,70 may be made sharp by the attachment of penetrating members or first and second stab plates 96, 97 thereon. First and second stab plates 96, 97 can be then attached to the first and second sliders 60, 70 by placing first and second stab plates 96, 97 over first and second stab posts 64a, 74a and then placing the assembled stab plates 96, 97 and first and second sliders 60, 70 into the hollow shaft 92 to form a shaft sub-assembly. This method of stab plate retention is best shown in FIG. 14. Stab plates 96, 97 can be used to pierce tissue during the placement of a fastener 105 into tissue and can be made from a rigid material such as stainless steel.

Next, the shaft sub-assembly can be placed into an fastener feeding station (not shown) and the fastener 105 can be fed one at a time into the first and second fastener guides 66, 76 and into the hollow channel formed from fastener channels 65, 75. The fastener 105 can be inserted until the fastener 105 engages with the feeding mechanism, which will be described later. Once the fastener 105 is in place, the first and second sliders 60, 70 can be reciprocated proximally and distally relative to one another to feed or index the fastener 105 further into the shaft sub-assembly. This process can be repeated for each new fastener 105 until the first and second sliders 60, 70 are fully loaded with a plurality of fasteners 105 in a serial fashion. The plurality of fasteners 105 can be equally spaced along the entire length of the first and second sliders 50, 60. The shaft sub-assembly containing the fastener 105 may be then placed into the right handle half 41. Shaft 92 can be received in shaft slot 44 and the guide ribs 68 of the first slider 60 may be slidably placed into the guide slot 46. Next, a lockout wheel 100 may be placed into a wheel receptacle 48 located within the right handle half 41 at a position proximal to the pivot bore 47.

A trigger assembly can be constructed by placing a trigger plate 87 and a lockout arm 88 over a pivot 86 that extends laterally on either side of trigger 85 and fixably attaching them to trigger 85 with a pair of pins 89. A drive arm 90 can extend upwardly from the trigger plate 87 and a spring post 91 can extend from the far side of the trigger plate 87 towards the right handle half 41. An end of a trigger spring 104 (FIG. 3) can be then placed over spring post 91. The trigger assembly may be then placed into the right handle half 41 by placing the far side pivot 86 (not shown) into a pivot bore 47. Trigger 85, trigger plate 87, and lockout arm 88 are shown as separate pieces but can alternately be constructed as a single piece from an engineering thermoplastic such as polycarbonate, styrene or the like.

FIG. 3 shows the fully assembled elements of the handle 40. Prior to the view shown in FIG. 3, the free end of the trigger spring 104 has been stretched and attached to a spring pin 49 of the grip 43. The attachment of the free end of the trigger spring 104 tensions trigger spring 104, and biases the trigger 85 to the open position shown. Next, a first return spring 115 may be compressed and placed into a first spring pocket formed between the first spring stop 67 of the first slider 60 and a first spring rib 50 of the handle halves 41, 42. A second return spring 116 may be also compressed and placed into a second spring pocket formed between the second spring stop 77 of the second slider 70 and a second spring rib 51. Finally, the left handle half 42 may be attached to the right handle half 41 to complete the assembly of the surgical instrument 35. The left handle half 42 has been removed for clarity.

The Actuator Mechanism

The instrument of FIGS. 3–8 shows the operation of the actuator or sequencing mechanism that can control the timing and movement of elements within the surgical instrument 35. The actuator mechanism can be engaged by the actuation of the trigger 85 and moves the drive mechanism or first and second sliders 60,70 into at least three sequential positions. Actuation of the trigger 85 can simultaneously move the first and second sliders 60, 70 distally from a first proximal position to a second distal position, then returns the first slider 60 to the proximal position, and finally returns the second slider 70 to the proximal position. This sequence of motion can advances the plurality of fasteners 105 distally, and deploys the distal end of the fastener into tissue in two steps. The actuator mechanism can consists of the latch 55; the trigger assembly described above, the first and second return springs 115, 116, and the first and second sliders 60, 70.

FIG. 3 shows a first or left side view of the surgical instrument of FIG. 1 with the right handle half 41 in place, the left handle half 42 removed for clarity, and the trigger 85 in the initial open position. The first and second sliders and second return springs 115, 116 can bias the first and second sliders 60, 70 distally within the handles 41, 42. The trigger 85 of the trigger assembly can be in the full open position with the drive arm 90 poised to operatively engage a proximal end of the guide rib 68 of the first sequencing member 62. First and second sliders 60, 70 are in the first proximal position.

Figure 4:
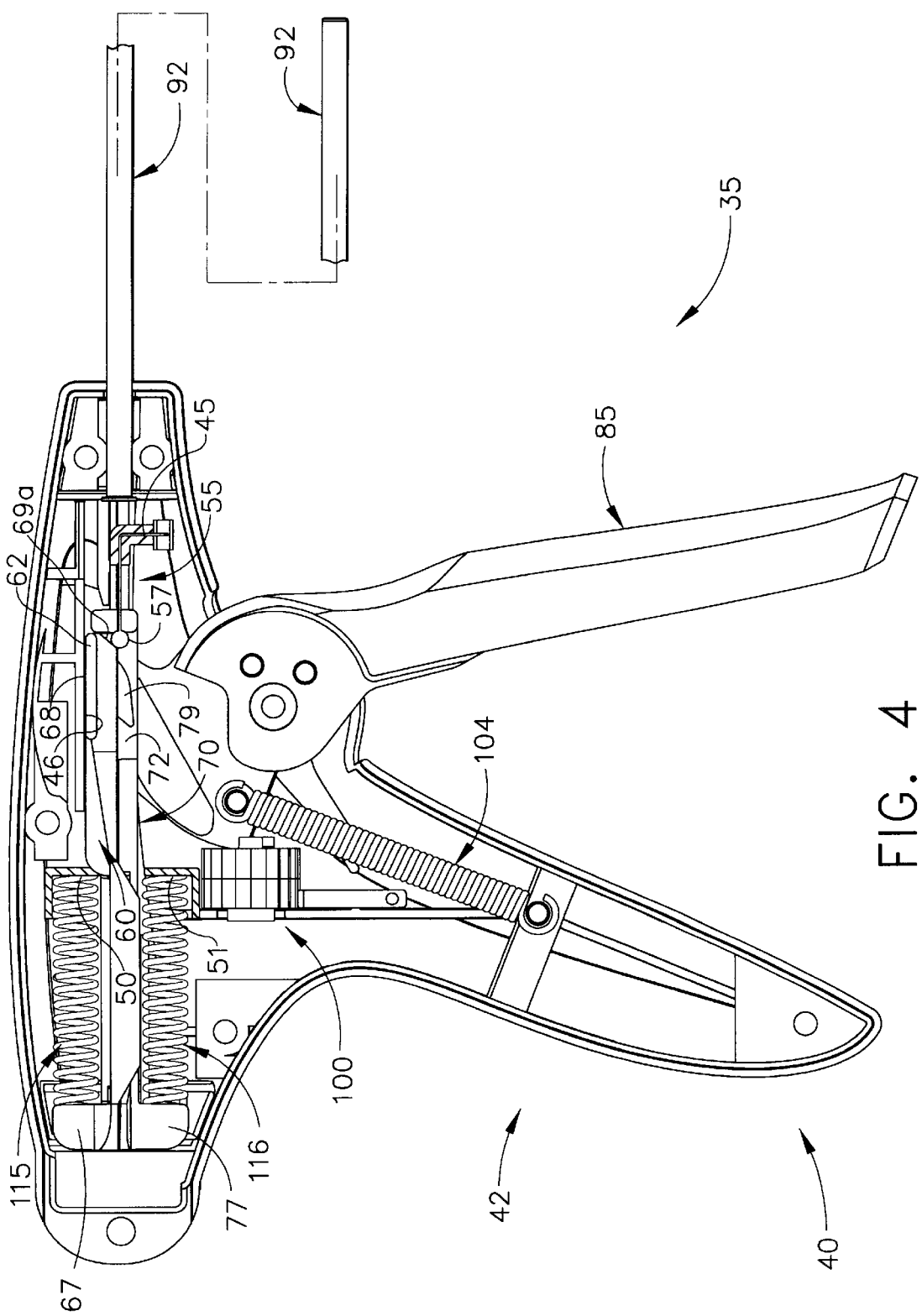
FIG. 4 is a side view of a second side of the surgical instrument of FIG. 3 with the left handle half in place and with the right handle half removed, showing all of the internal elements therein and the trigger in an open position.

FIG. 4 shows the second or right side view of the surgical instrument of FIG. 3 with the left handle half 42 in place and with the right handle half 41 removed. The latch 55 is visible in this view, and the latch post 57 of latch 55 may be operatively engaged with a first ramp 69a located on the distal end of the first sequencing member 62. A portion of the first and second spring ribs 50, 51 and the latch slot 45 of the right handle half 41 are shown in cross-section for clarity.

Figure 5:
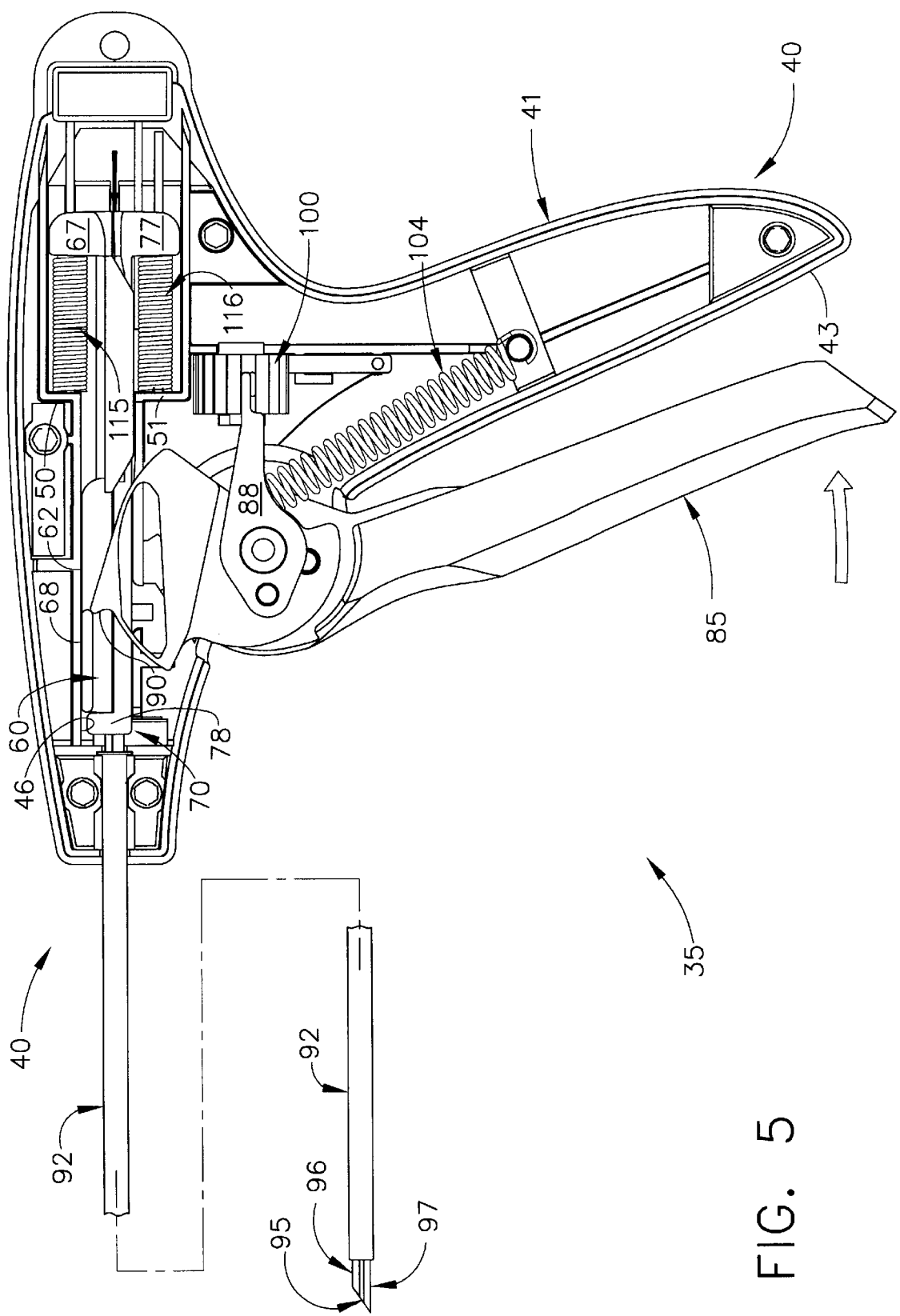
FIG. 5 is a side view of the first side of the surgical instrument of FIG. 3 wherein the trigger is moved to a partially closed position to partially move the first and second sliders and to partially extend the end effector from the surgical instrument.
Figure 6:
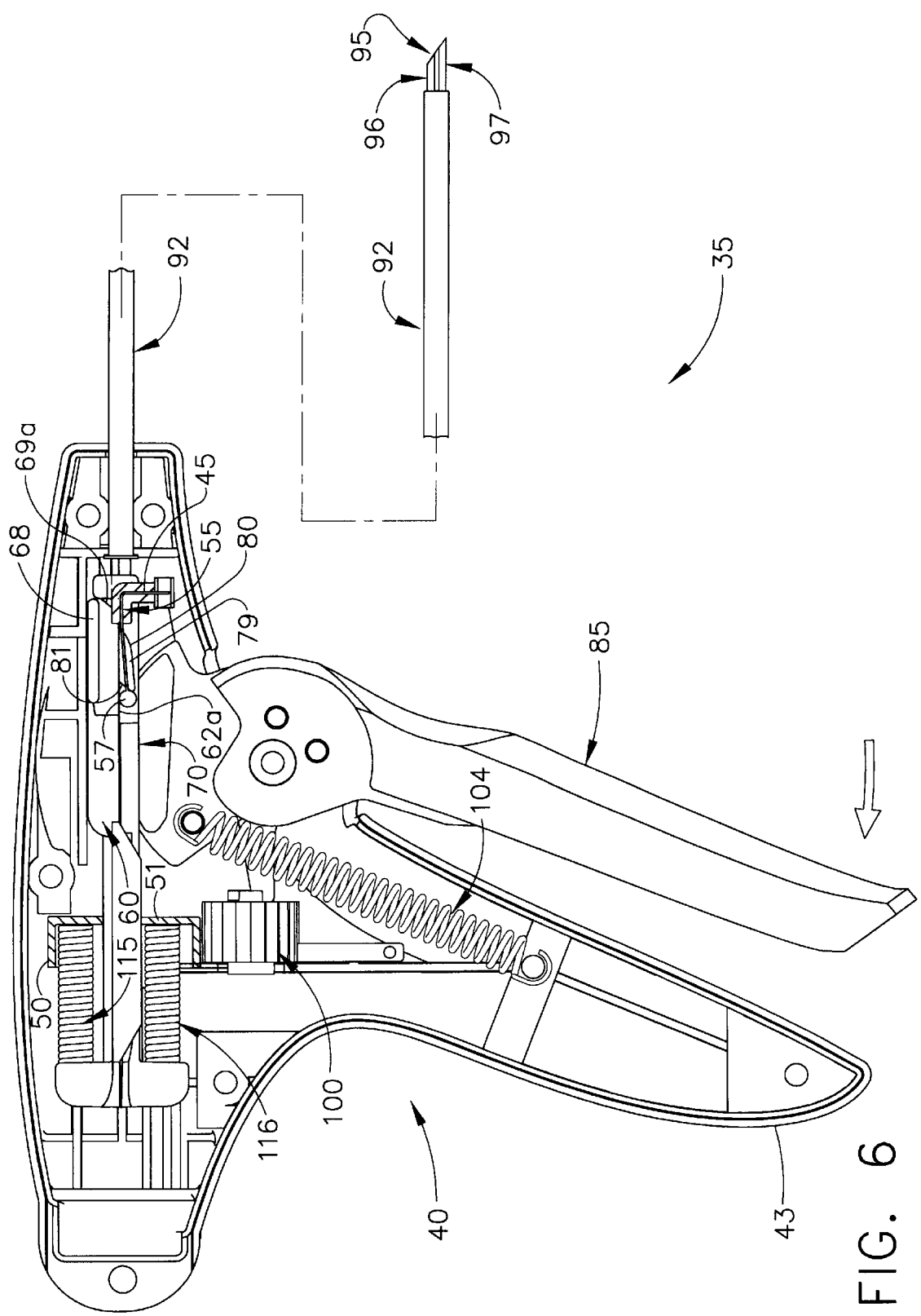
FIG. 6 is a side view of the second side of the surgical instrument of FIG. 5, wherein the trigger is moved to a partially closed position to extend the end effector from the surgical instrument.

FIGS. 5 and 6 show the left and right side views of the assembled surgical instrument 35 respectively, and show the first and second sliders 60, 70 can be translated or moved distally from the first position of FIGS. 3–4 to the second position by the trigger 85. The distal movement of first and second sliders 60, 70 can extend the end effector 95 from the distal end of the shaft 92. The trigger 85 is in a first partially closed position and may be poised to release the first slider 60 from the drive arm 90 of the trigger assembly.

In FIG. 5, as trigger 85 rotates counter-clockwise towards the grip 43, the drive arm 90 can rotate into operative engagement with the guide rib 68 and move the first slider 60 distally. As first slider 60 moves distally, the forked stops 78 of the second slider 70 may be contacted, pushing the second slider 70 distally. The distally moving first and second sliders 60, 70 can compress the first and second return springs 115, 116 as shown. The lockout arm 88 of the trigger assembly is moving upwardly, and can rotating the lockout wheel 100.

In FIG. 6, as the first and second sliders 60, 70 move distally, they can deflect the latch post 57 of the latch 55 downwardly to slide along the first ramp 69a of the first slider 60 and a second ramp 80 of the second slider 70. Latch post 57 of the latch 55 can pass the second ramp 80 and deflect upwardly to lock against a third ramp 81 of the second slider 70 and against a bottom surface 62a of the first sequencing member 62. With the latch 55 in this position, the second slider 70 can be locked in the distal position and cannot move proximally.

Figure 7:
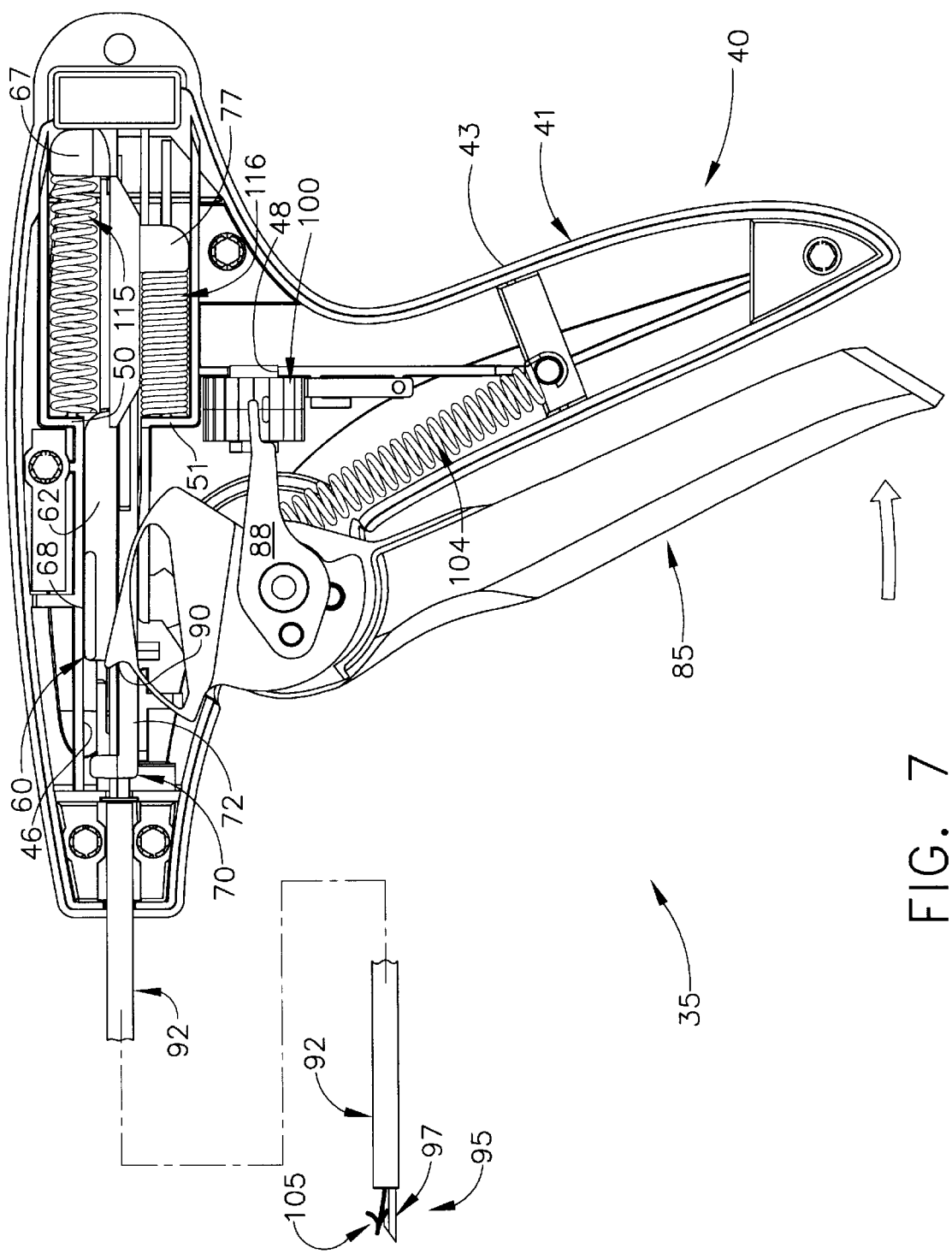
FIG. 7 is a side view of the first side of the surgical instrument of FIG. 5 wherein the trigger is moved to a fully closed position to retract a first portion of the end effector attached to the first slider into the surgical instrument, and to expose a portion of a fastener at the end effector.
Figure 8:
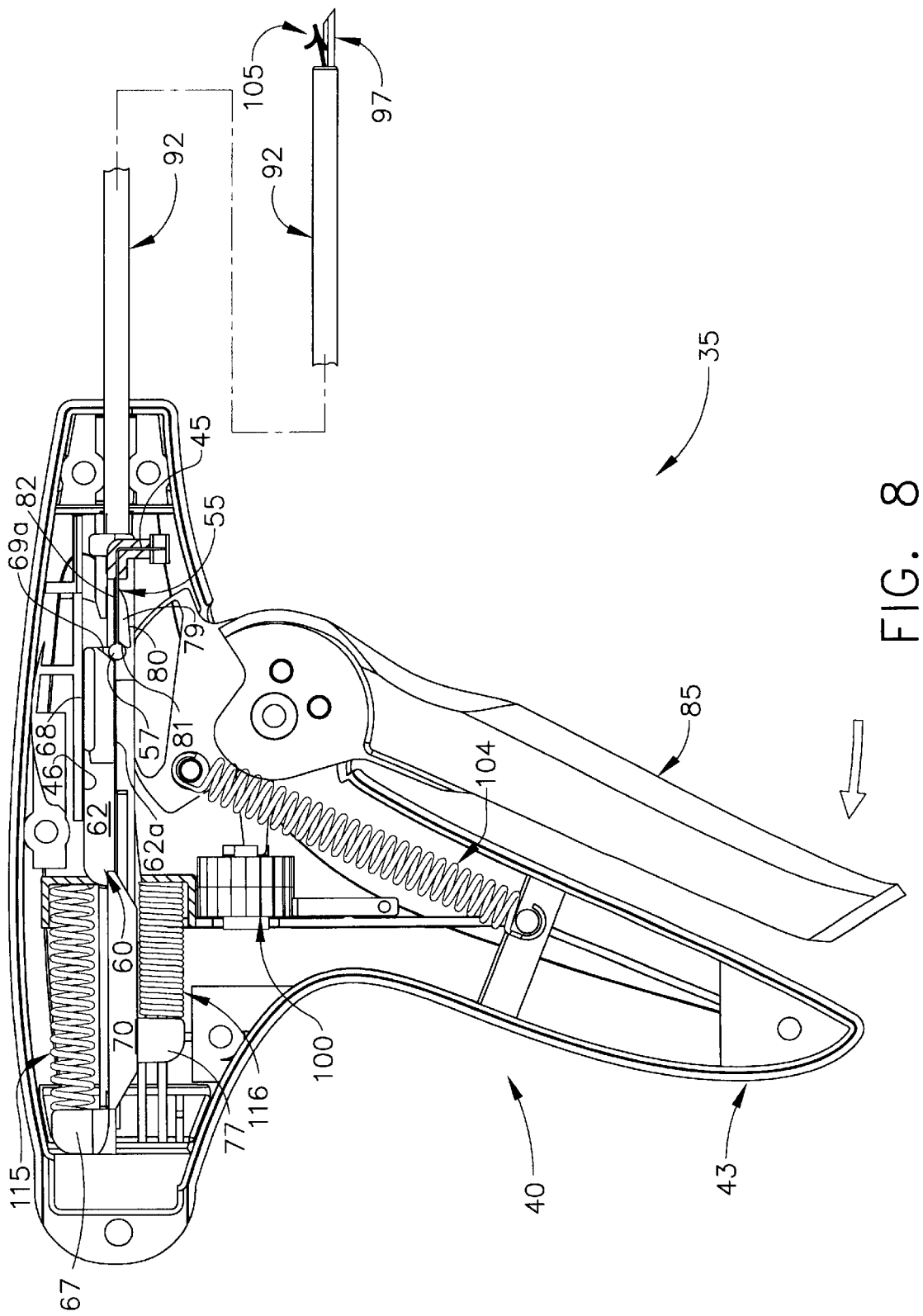
FIG. 8 is the view of the second side of the surgical instrument of FIG. 7, wherein the trigger is moved to a fully closed position to retract an upper portion of the end effector attached to the first slider into the surgical instrument, and to expose a portion of a fastener at the end effector.

FIGS. 7 and 8 show the left and right side views of the assembled surgical instrument 35 respectively, after the first slider 60 has reciprocated or returned back to the first proximal position of FIGS. 3 and 4 to partially release a fastener 105 from the end effector 95.

As shown in FIG. 7, after the guide rib 68 may be released from the drive arm 90, the first slider 60 reciprocates distally to the first proximal position from the second distal position shown in FIGS. 5 and 6. Slider 60 may be returned to the proximal position by first return spring 115. The proximal movement of the first slider 60 can retract the first stab plate 96 proximally into the shaft 92 and release a distal end of the fastener 105 as shown. The lockout arm 88 can move upwardly from and disengaged with the lockout wheel 100.

In FIG. 8, as first sequencing member 62 moves proximally, the bottom surface 62a of the first sequencing member 62 can moves distally away from the latch post 57 enabling the latch 55 to deflect upwardly to the un-deflected position shown in FIG. 3. This movement can unlock the second sequencing member 72. With the second sequencing member 72 unlocked, the compressed second return spring 116 may reciprocate the second slider 70 back to the original proximal position of FIG. 3. As the second slider 70 reciprocates back to the first proximal position, latch post 57 may be deflected upwardly by the third ramp 81 of the cam plate 79 to travels over a top surface 82 of the distally moving cam plate 79 and returns to the position of FIG. 3. At this point, if an instrument lockout is not actuated, the trigger 85 can be released to bring the elements of the instrument back to the positions shown in FIG. 3.

The Fastener

FIGS. 9–13 are expanded views showing the novel surgical element, anchor, or fastener 105 of the present invention. A plurality of fasteners 105 of the present invention are contained serially within the surgical instrument 35 (FIG. 2B) and are used to fasten or suture a prosthetic such as a surgical mesh pad onto tissue. The fastener 105 of the present invention may be elastic and is shown in its original unconstrained state in FIGS. 9 and 10. When fastener 105 may be distorted or constrained, it will return to its original shape when released. Fastener 105 can be formed or stamped from a sheet or foil of a pseudoelastic or superelastic nickel titanium alloy to take advantage of pseudoelastic or superelastic properties thereof, or an elastic or spring grade of steel, stainless steel, copper, or other titanium alloys.

Most preferably, fastener 105 may be made from an alloy comprising from about 50.5% (as used herein these percentages refer to atomic percentages) Ni to about 60% Ni, and most preferably about 55% Ni, with the remainder of the alloy Ti. Preferably, the fastener may be such that it may be superelastic at body temperature, and preferably has an Af in the range from about 15° C. to about 37° C. The superelastic design of the fastener 105 makes it crush recoverable which makes it possible to store a large fastener 105 within a small diameter shaft 92.

As mentioned above, fastener 105 of the present invention may be made from a superelastic alloy and can be made of an alloy material having greater than 50.5 atomic % Nickel and the balance titanium. Greater than 50.5 atomic % Nickel allows for an alloy in which the temperature at which the martensite phase transforms completely to the austenite phase (the Af temperature) may be below human body temperature and may be about 15° C. to about 37° C. so that austenite may be the only stable phase at body temperature.

Figures 9, 10:
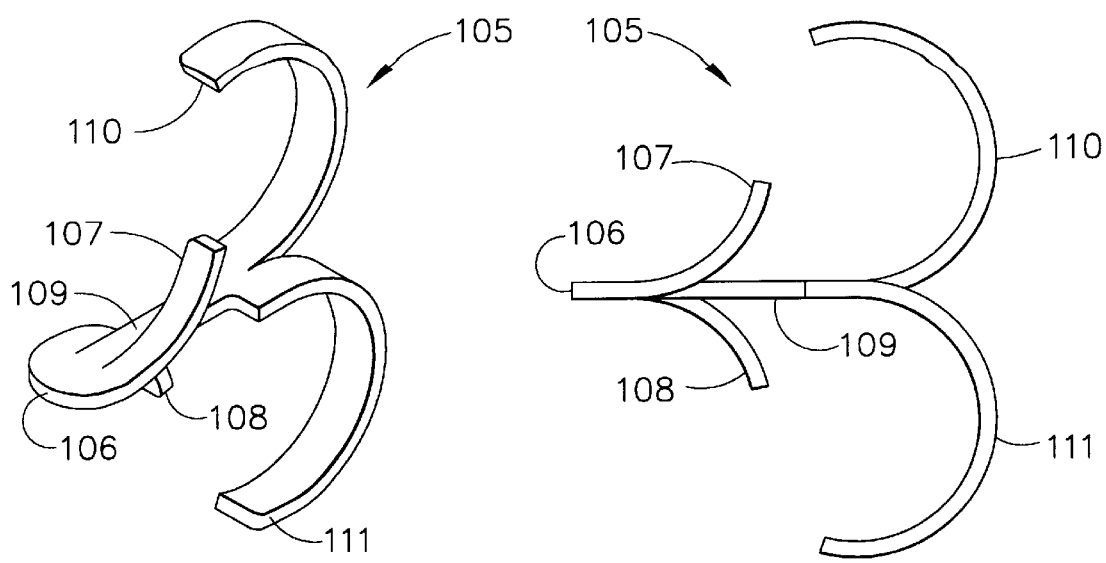
FIG. 9 is an isometric view of a fastener of the present invention wherein the fastener has a pair of distal barbs and a pair of longer proximal legs, the fastener is shown in an unconstrained state.
FIG. 10 is a side-view of FIG. 9 wherein the fastener of the present invention is shown in an unconstrained state.

The unconstrained fastener 105 of FIGS. 9 and 10 can have a generally planar continuous body member 109 having a first (distal) end and a second (proximal) end. At least one barb can extend from the distal end, and at least two barbs extend from the proximal end. The continuous body member 109 can have a distal tip 106 which may be rounded or blunt. Alternately, the distal tip 106 of the fastener 105 can be made sharp or pointed if desired. A first and a second barb 107,108 can extend proximally and axially away from the distal tip 106 and away from the body member 109. The first and second barbs 107,108 can be curved. The distal end of the body member 109 can a pair of barbs or a first and a second leg 110,111 that extend distally from the body member 109 and away from each other in different directions. First and second legs 110,111 of the present invention may engage the inner surfaces of the first and second members 60,70, can also be curved outwardly from the body member 109, and can form the everted configuration f FIGS. 9 and 10. The ends of the first and second barb 107,108, and first and second leg 110,111, can be blunt.

Figure 11:
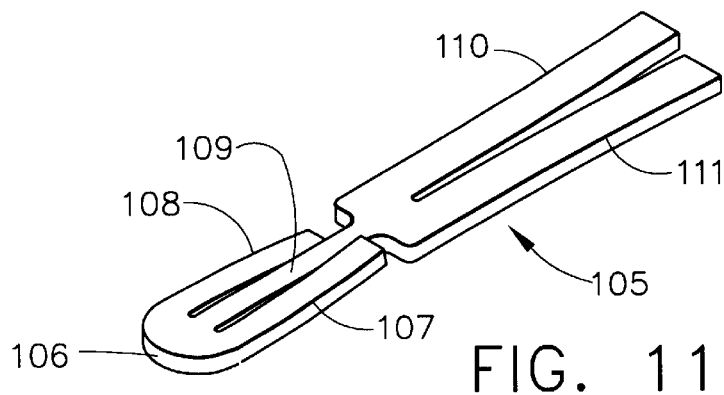
FIG. 11 is an isometric view of the fastener of FIG. 9 wherein the fastener of the present invention is shown in a constrained state as found within the surgical instrument of FIG. 1.
Figure 12:
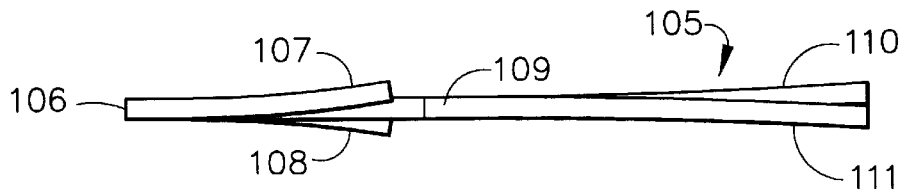
FIG. 12 is a side-view of FIG. 11 wherein the fastener of the present invention is shown in a constrained state.
Figure 13:
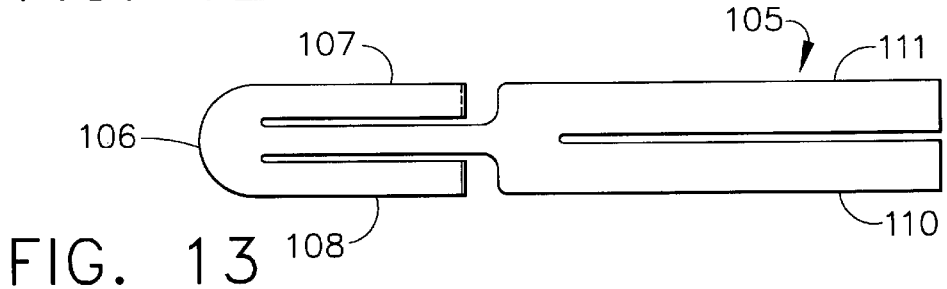
FIG. 13 is a bottom-view of FIG. 12 wherein the fastener of the present invention is shown in a constrained state.

FIGS. 11–13 shows an isometric view, a side view, and a bottom view of the fastener 105 of the present invention wherein the fastener 105 is shown in a constrained state that the fastener 105 assumes when stored within the surgical instrument 35 (FIG. 1). The fastener 105 can revert to the unconstrained shape of FIGS. 9 and 10 when released from the surgical instrument 35. Surgical fastener 105 can also be used as a marker when placed in tissue. That is, the material of the fastener 105 may be such that it appears in diagnostic tests such as MRI scans, CAT scans, X-rays, or ultrasound, and the surgeon can readily identify the location of the fastener relative to other body features.

The Drive Mechanism

FIGS. 14 and 15 are enlarged partial cross-sectional views of the distal end of the shaft 92 of FIG. 3 showing the first and second sliders 60,70 or walking beams at the first or un-actuated position wherein they are recessed into the shaft 92, and the fasteners 105 contained therebetween. At the first distal position, the trigger 85 of the surgical instrument 35 may be filly open (FIG. 3) and the sawteeth 120 of the first slider 60 may be lined up with and directly opposed from the sawteeth 120 within the second slider 70. FIG. 15 shows how the first and second fastener channels 65, 75 can form a passageway for the reception of the fasteners 105 therein.

The drive mechanism uses the fasteners 105 themselves as a part of the drive mechanism. As shown in FIG. 14, the drive mechanism 59 can have three distinct elements: the first member or slider 60, the second member or slider 70, and the plurality of fasteners 105 stored in a serial fashion therebetween. Fasteners 105 may be held between the sawteeth 120 with the barbs 107, 108 deflecting outwardly to center the fasteners 105 between the sawteeth 120. First and second legs 110, 111 of the fasteners 105 may be biased outwardly, contacting the surfaces of the sawteeth 120 at an angle as shown. The corners of the legs 110, 111 where they contact the first and second sliders 60,70 can dig into and attempt to expand outwardly against the sawteeth if the fasteners 120 are moved proximally relative to the first or second slider. Also the distal ends of the legs can form positive contact with the steps 121 of the sawteeth 120. Distal movements of the fasteners within the first and second sliders 60,70 can slide the corners of the legs 110, 111 along the inclines 122. Additionally, the corners of the barbs 107, 108 contact the inclines 122 and can act in a similar manner as the legs 110, 111 when they engage the first and second sliders 60,70. The distal ends of the first and second legs 110, 111 are shown positioned within the pockets at the junction of the step 121 and the incline 122, and are operatively engaged with the steps 121 and slidingly engaged with the inclines 122. It can be the positive contact or engagement of the fasteners 105 with the steps 121 and sliding contact or engagement with the inclines 122 that drives or feeds the plurality of fasteners 105 between the reciprocating first and second sliders 60,70 and places the fastener 105 into tissue. Thus, both the barbs 107, 108 and the legs 110, 111 can propel the fasteners.

It can be seen that given the elements of the drive mechanism 59 described above, distal movement of both of the first and second sliders 60, 70 can result in operative engagement of the fasteners 105 with the steps 121 of both sliders 60, 70. This operative engagement with the distally moving sliders 60, 60 can result in distal movement of the fasteners 105. If one of the sliders such as first slider 60 is moved distally while the other remains stationary, the fasteners 105 may operably couple with and move with the moving slider 60, while slidingly engaging with the stationary slider 70. And, if one of the sliders such as first slider 60 moves proximally while the other remains stationary, the fasteners 105 can operatively engage with the stationary slider 70 and remain stationary and slidably engaged with the moving slider 60.

With the above combinations of motions and reactions, there are three different sequences of motion possible with the sliders 60, 70 that will drive the fasteners 105 distally through the surgical instrument 35 (FIG. 3). One of these sequences of motion was selected for use with the surgical instrument 35, as it can place a fastener 105 into tissue. This driving sequence using the drive mechanism 59 is shown in a step by step manner beginning with the start position shown in FIG. 14, and finishing in FIGS. 18–22. The other two driving sequences will be described later.

The actuator mechanism of the present invention can have at least three sequential positions. First, the actuator mechanism can move the first and second sliders 60, 70 distally (FIGS. 18, 19) from a first proximal position (FIG. 14) to a second distal position (FIG. 19). This movement can positively engage the fasteners 105 with the first and second sliders 60, 70 and move the fasteners 105 distally from the first position to the second position. Moving both the first and second sliders 60, 70 (FIG. 14) from a first proximal position to a second distal position to move the entire plurality of fasteners 105 distally within the surgical instrument 35. That is, each fastener 105 (with the exception of the distal most fastener 105) may now occupies the position of the preceding fastener 105.

Figure 20:
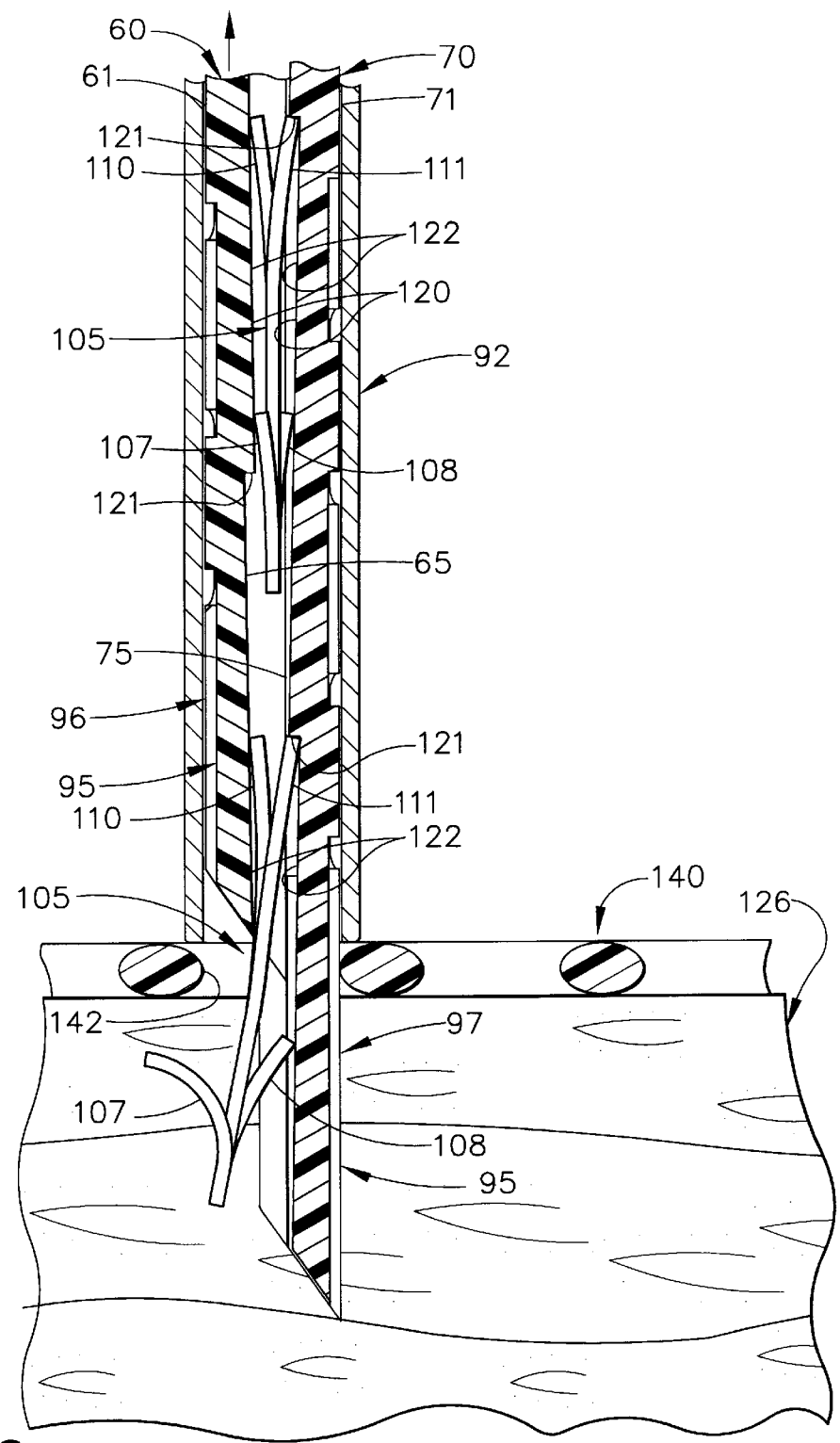
FIG. 20 is a cross-sectional side view of the inguinal floor and instrument of FIG. 19 wherein a first portion of the end effector is partially retracted into the shaft to deploy a first barb of the fastener of the preferred invention contained therein and to engage the first barb with the inguinal floor.
Figure 21:
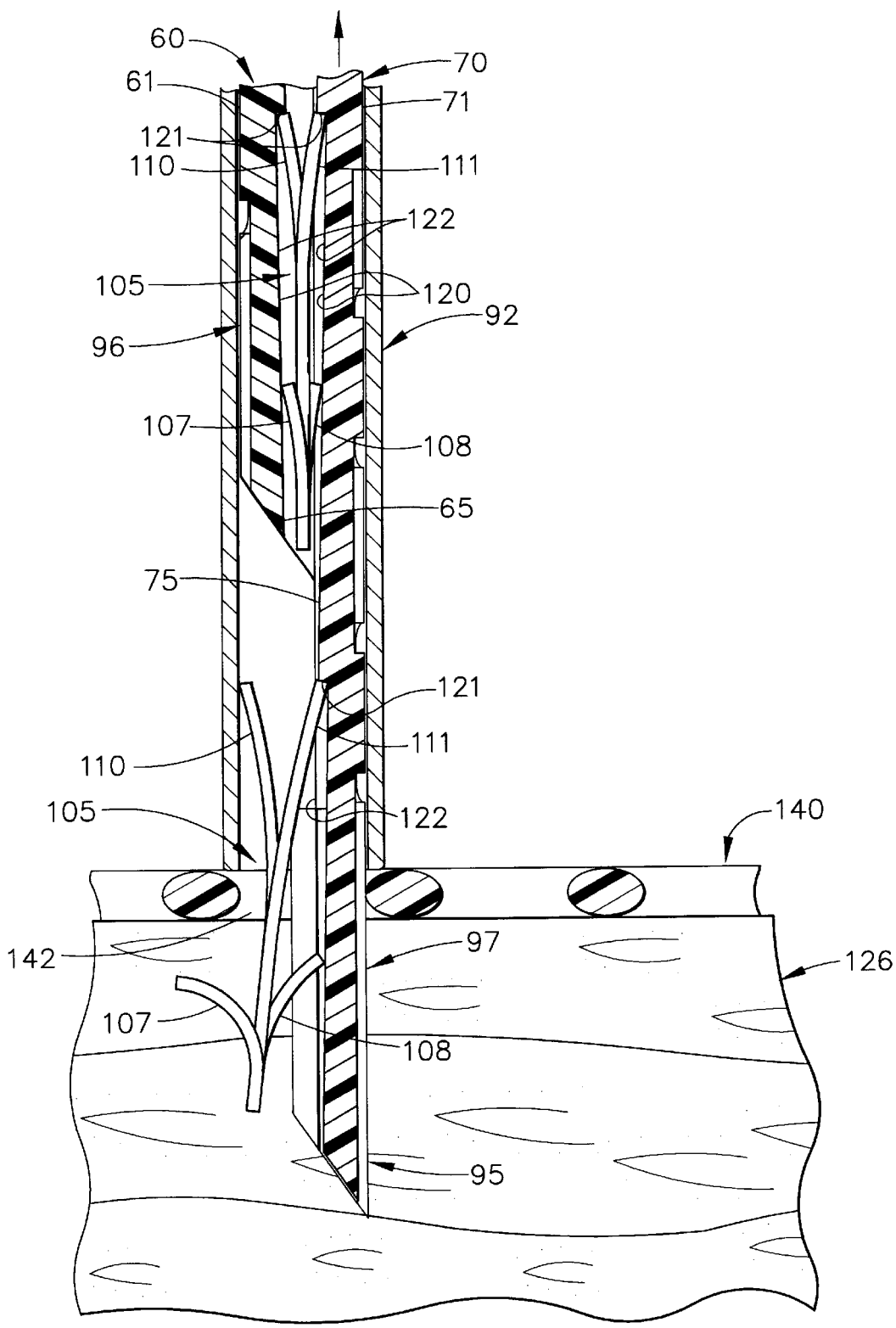
FIG. 21 is the cross-sectional side view of FIG. 20 wherein the first portion of the end effector of the present invention is fully retracted into the shaft, the full retraction releasing the arms of the fastener of the preferred invention into the portion of the shaft previously occupied by the first portion of the end effector.

Next, as shown in FIGS. 20, 21, the actuator mechanism can move or reciprocate the first slider 60 proximally from the second distal position back to the first proximal position to opposedly align the sawteeth 120 of the first and second sliders 60, 70. As shown, the fasteners 105 may be operatively engaged with the stationary second slider 70 and remain stationary (longitudinally) within the shaft 92.

Figure 22:
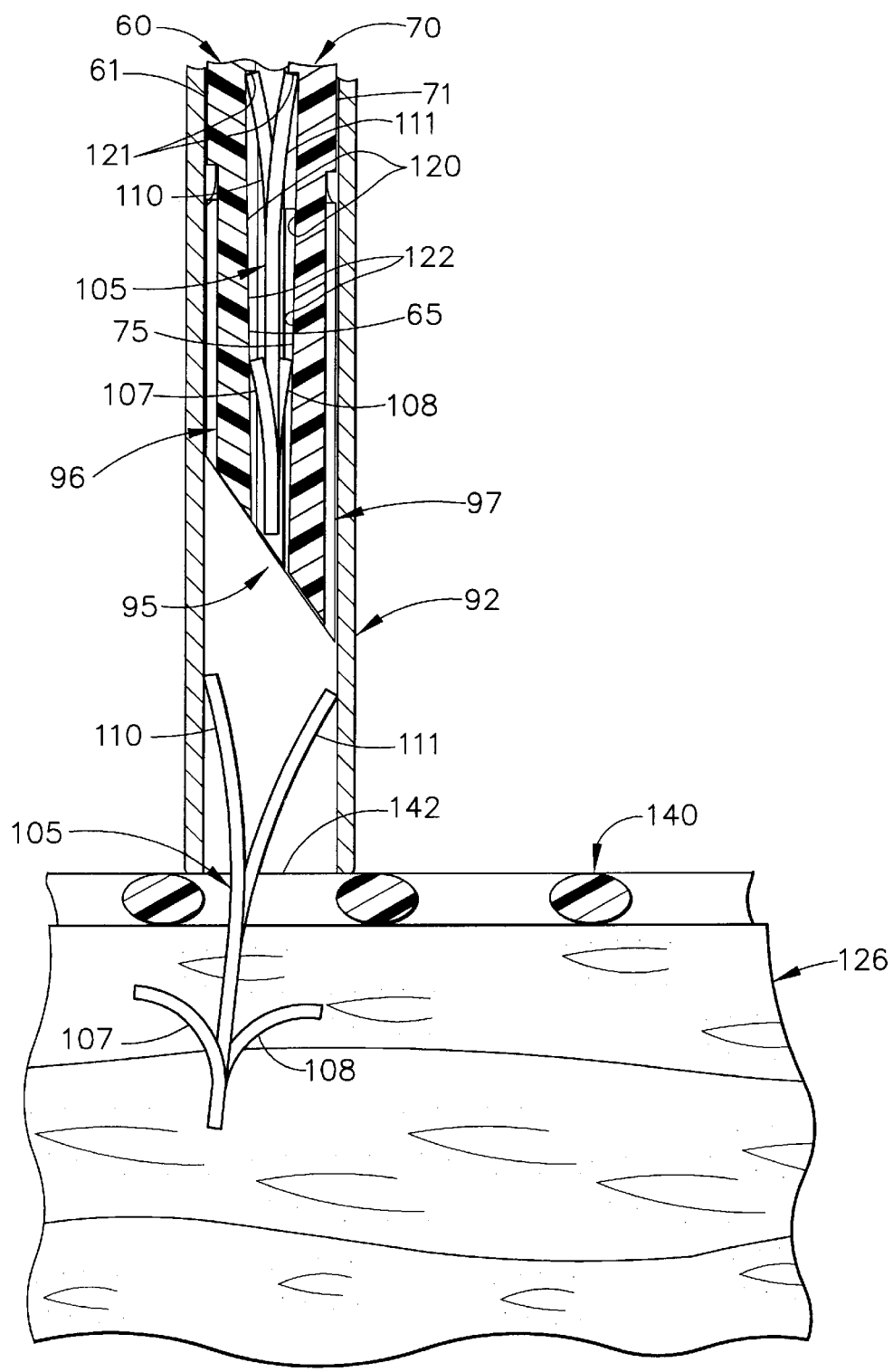
FIG. 22 is the cross-sectional side view of FIG. 21 wherein a second portion of the end effector of the present invention is fully retracted into the shaft, the full retraction engaging a second barb of the fastener of the present invention with the inguinal floor and both arms with the shaft.

Finally, as shown in FIG. 22, the actuator mechanism can move or reciprocate the second slider 70 proximally from the second distal position back to the first proximal position, and may realign the sawteeth 120 within the first and second sliders 60, 70. The fasteners 105 can be in operative contact with the stationary first slider 60 and remain stationary and in sliding contact with the distally moving second slider 70. As shown in FIG. 22, the first and second sliders 60, 70 can place the distal most fastener 105 within tissue and can move distally back to the first position. A new fastener 105 is shown within first and second sliders 60, 70, ready for placement within tissue.

As described above, there are two additional embodiments of the present invention wherein different sequences of motion are possible with the first and second sliders 60, 70. These alternate sequences of motion will also drive the fasteners 105 distally through the surgical instrument 35 (FIG. 3).

In the next or second embodiment, the sequence of motion may be to fix one of the first or sliders such as first slider 60 and to reciprocate the remaining slider 70 distally from the first position to the second position and back to the first position. In the third embodiment, the sequence of motion may be altered wherein the first and second sliders 60, 70 are reciprocated in opposite directions at the same time.

FIGS. 30–37 shows an alternate surgical instrument 235 of the present invention that uses the second embodiment of the drive mechanism described above wherein one of the sliders may be fixed, and one of the sliders reciprocates or moves to drive the fasteners 105 distally through the alternate surgical instrument 235. It is the relative motion between one moving slider and one fixed slider that can move the fasteners 105 distally, and either slider can be the moving slider as long as the remaining slider is fixed. To avoid confusion with the previously described elements such as sliders 60, 70, the changed elements of the alternate feeding mechanism 259 will be given new element numbers and descriptions where required. For example, the upper slider will be referred to as moving slider 260 and the lower slider will be referred to as fixed slider 270. The fasteners 105 and other elements that can be substituted in any embodiment of the surgical instrument will retain the same element numbers. Thus, the alternate feeding mechanism 259 can have three distinct elements: the moving slider 260, the fixed slider 270, and the plurality of fasteners 105 stored in a serial fashion in channels (FIGS. 34–37) therebetween. Due to the motion and sequencing differences, some additional mechanical differences and method of fastener placement can be required with the alternate feeding mechanism 259. These differences will be described below.

Figure 30:
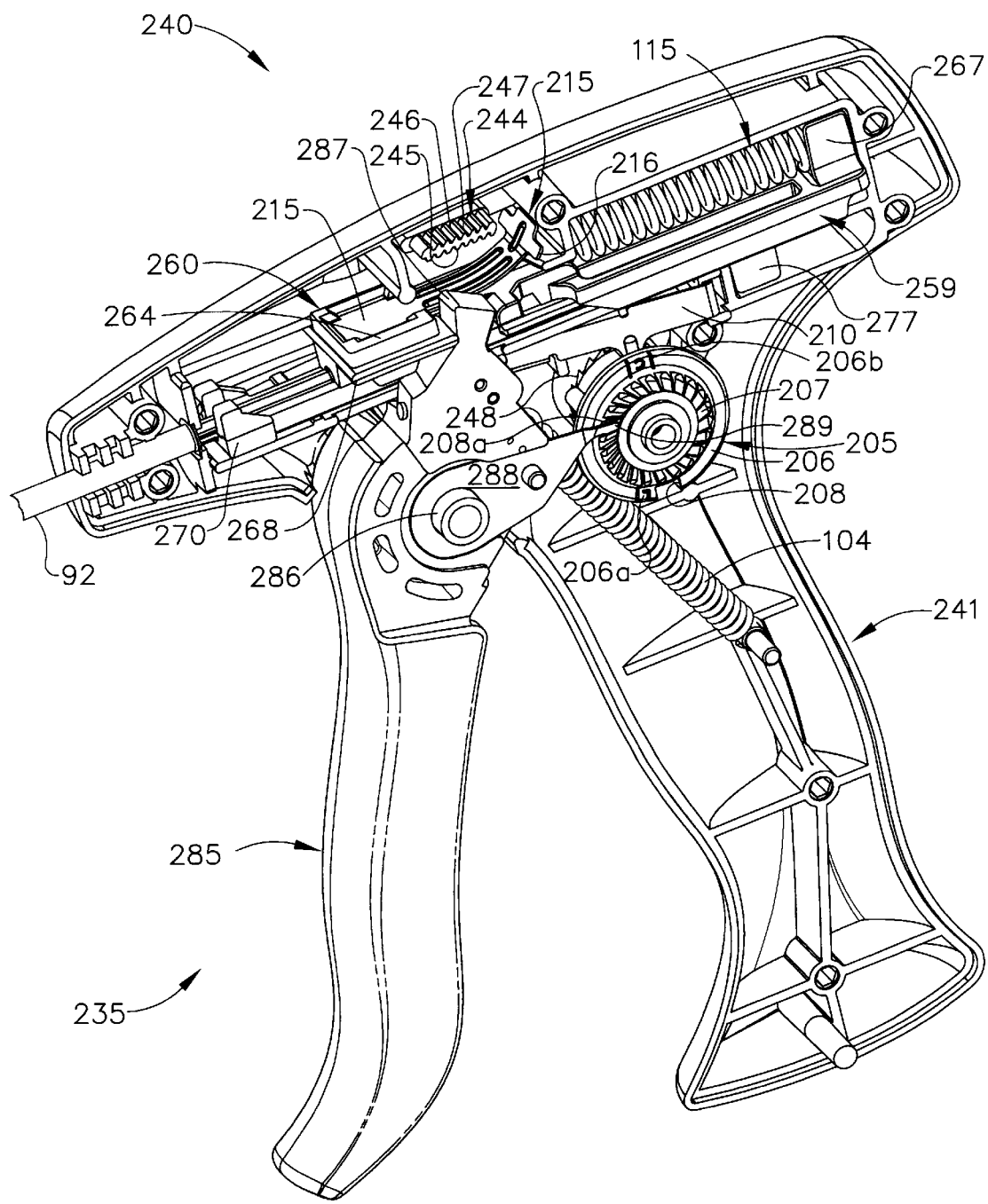
FIG. 30 is an isometric view of an alternate surgical instrument of the present invention wherein a left handle half is removed to show the elements within and the alternate surgical instrument has a fixed slider and a moving slider and an improved lockout mechanism.
Figure 31:
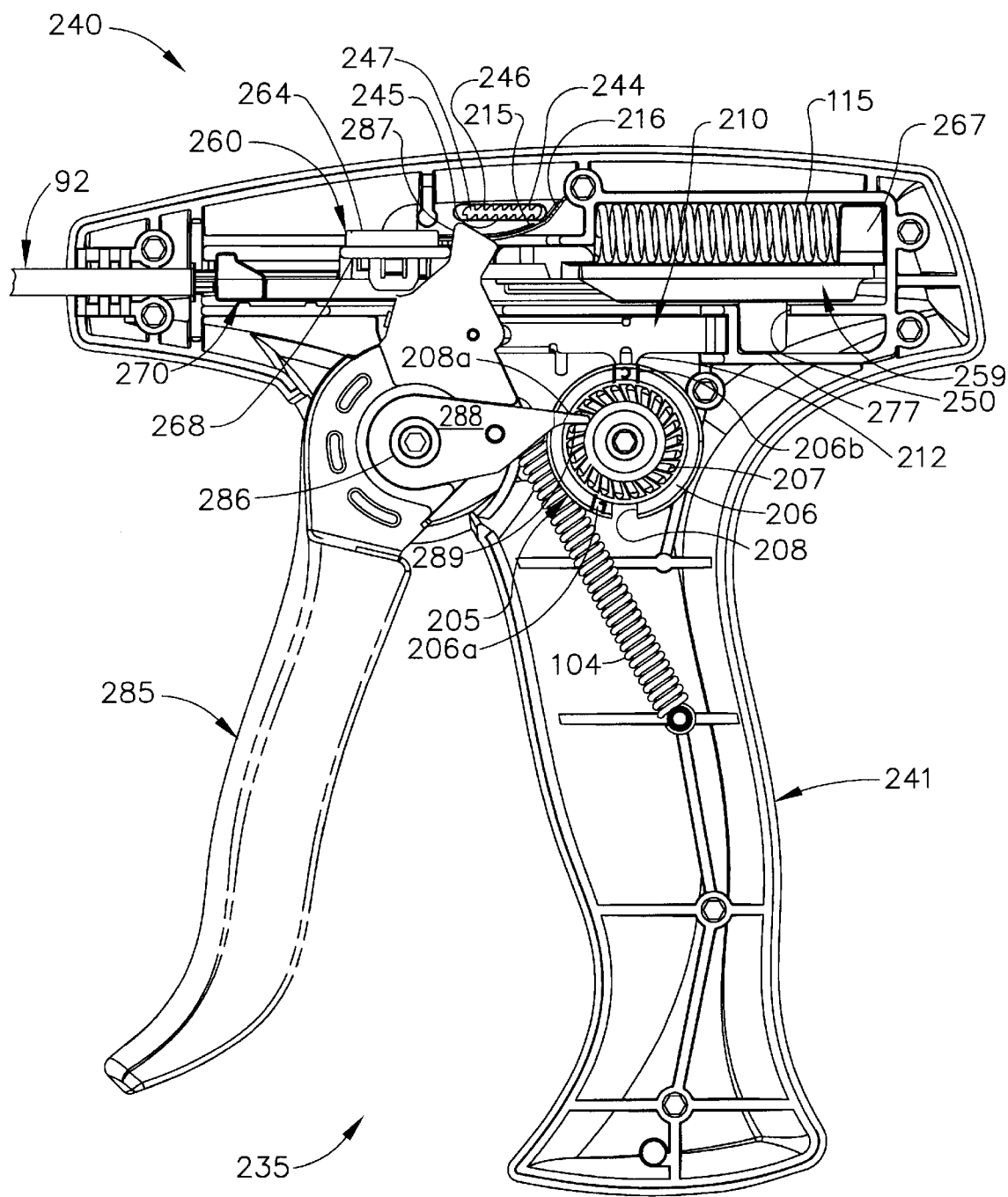
FIG. 31 is a side view of the handle of FIG. 30 wherein an alternate trigger is in a first open position and the moving and fixed sliders are in a first proximal most position.
Figure 32:
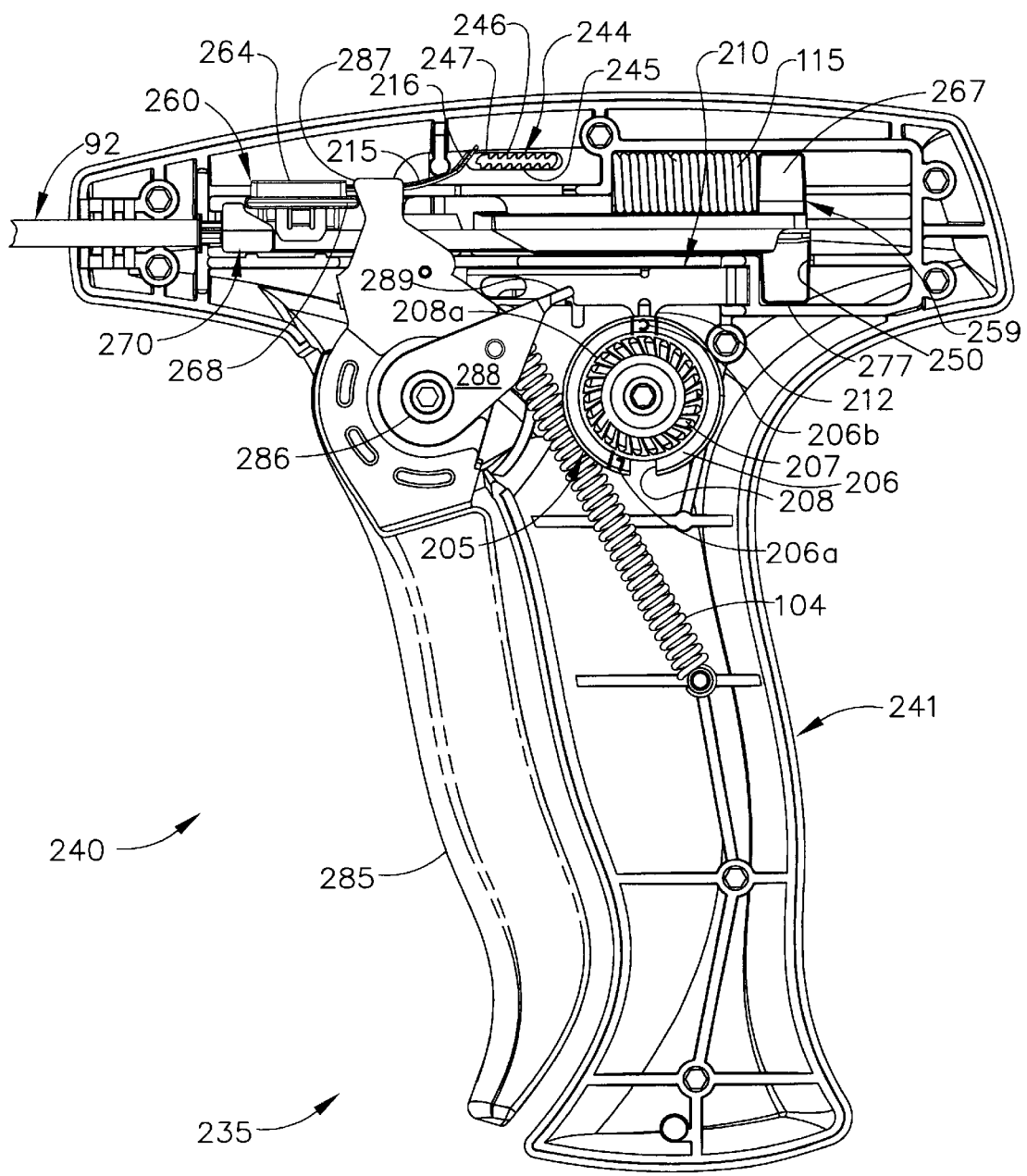
FIG. 32 is a side view of the handle of FIG. 31 with the trigger moved to a second closed position and the moving slider moved to a distal most position.
Figure 33:
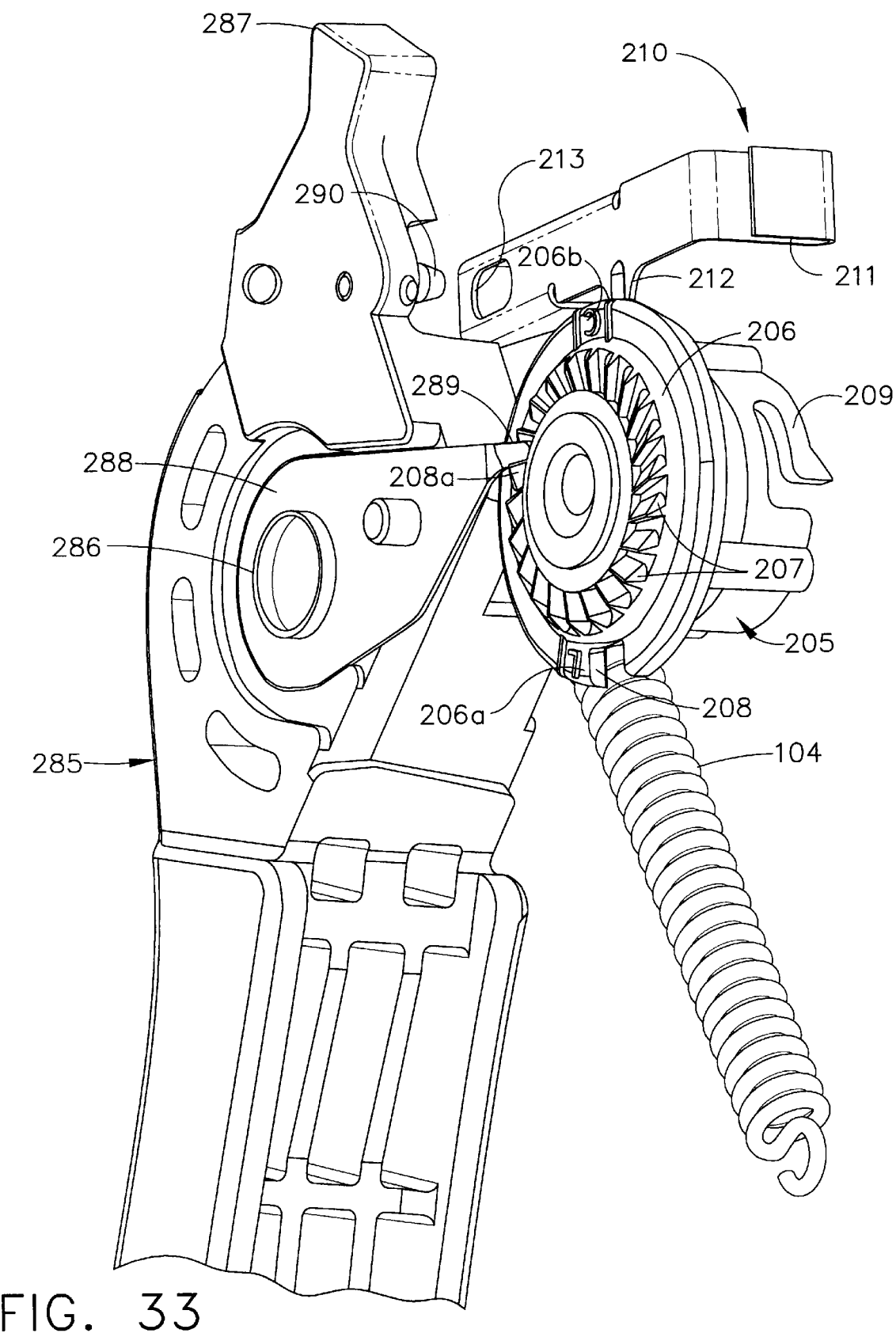
FIG. 33 is a is a fragmentary isometric view of an improved trigger lockout mechanism of FIG. 29 with a lockout arm fixably attached to the pivotable trigger, and operably coupled with a lockout wheel.

FIGS. 30–32 shows an alternate handle 240 of the alternate surgical instrument 235 and the elements thereof. For clarity, a left alternate handle half 242 of the alternate handle 240 has been omitted (i.e. not shown) so the placement and movement of the elements within a right alternate handle half 241 can be seen. FIGS. 34–37 show the movement of the sliders and other elements in a distal end of the alternate surgical instrument 235 as a fastener 105 may be applied to tissue to attach hernia mesh to tissue. FIG. 33 shows an alternate embodiment of a trigger lockout mechanism.

In FIGS. 30–32, the moving slider 260 may be located above the fixed slider 270 in the right alternate handle half 241 and extend distally into the tube 92 extending from a distal end of the alternate handle 240. First return spring 115 can bias the moving slider 260 proximally to the position shown in FIGS. 30–31 by pushing against a moving spring stop 267 of the moving slider 260. Moving slider 260 may be moveable distally within the alternate surgical instrument 235 by an alternate trigger 285 pivotably mounted within the alternate handle 240. Alternate trigger 285 can pivot around a pair of opposed alternate pivots 286 to bring an alternate drive arm 287 into contact with a guide rib 268 extending outwardly from the moving slider 260. Movement of the alternate trigger 285 from a first open position (FIG. 30–31) to a second closed position (FIG. 32) can move the moving slider 260 and fasteners 105 from a proximal most position shown in FIGS. 30–31 to a distal most position shown in FIG. 32. This motion can compress the first return spring 115 between the right alternate handle 241 and stretch a trigger spring 104 attached to the alternate trigger 285 and right alternate handle 241 (FIG. 32). Release of the alternate trigger 285 from the second closed position can enable the compressed first return spring 115 to return the moving slider 260 to the proximal most position and the trigger spring 104 to return the alternate trigger 285 to the first open position.

A governor 215 may be fixedly attached to a governor socket 264 on the moving slider 260 and can ensure one way movement of the alternate trigger 285 as it moves from the first open position to the second closed position. Once the alternate trigger 285 is fully closed, the governor 215 may be reset and ensure one way movement of the alternate trigger 285 as it moves from the second closed position and back to the fully open position. The actions of the governor 215 can ensure full proximal and distal reciprocation of the moving slider 260 relative to the fixed slider 270 and the advancement of the fasteners 105 therebetween. The governor 215 may be a spring and can have governor blades 216 extending laterally outward from a proximal end of the governor 215 to operatively engage with at least one governor rack 244 extending inwardly from the alternate handle 240. Governor rack 244 can be an inward extension of the plastic handle halves 241,242 or can be one or more pieces fixedly attached to the alternate handle 240.

In FIG. 31, the governor 215 is shown deflecting upwardly and below the governor rack 244. As the alternate trigger 285 is moved from the first open position of FIG. 31 and towards the second closed position of FIG. 32, the governor 215 may be moved distally and may be deflected downwardly by the governor rack 244. This motion can bring an upper edge of the governor blades 216 into contact with a lower rack 245 of rack sawteeth 247. The rack sawteeth 247 can be oriented to provide one way sliding engagement with the governor blades 216 during the full distal advancement of the moving slider 260 and the fasteners 105, and locking engagement if the moving slider 260 may be moved proximally by opening the alternate trigger 285. As shown in FIG. 32, the alternate trigger 285 is fully closed and the governor 215 may be reset upwardly by sliding out from under the lower rack 245. As the alternate trigger 285 is returned from the closed position to the open position, the moving slider 260 may move proximally to bring a lower edge of the governor blades 216 into contact with an upper rack 246 of the governor rack. The rack sawteeth 247 of the upper rack 246 may be oriented to provide one way sliding action with the governor blades 216 as the alternate trigger 285 moves from the closed position to the open position and to lockingly engage if the trigger 285 moves back towards the closed position. The governor rack 244 can be an inward extension of the plastic alternate handle 240 or can be a secondary part formed of an alternate material such as a metallic or a plastic.

The Anatomy

Figure 16:
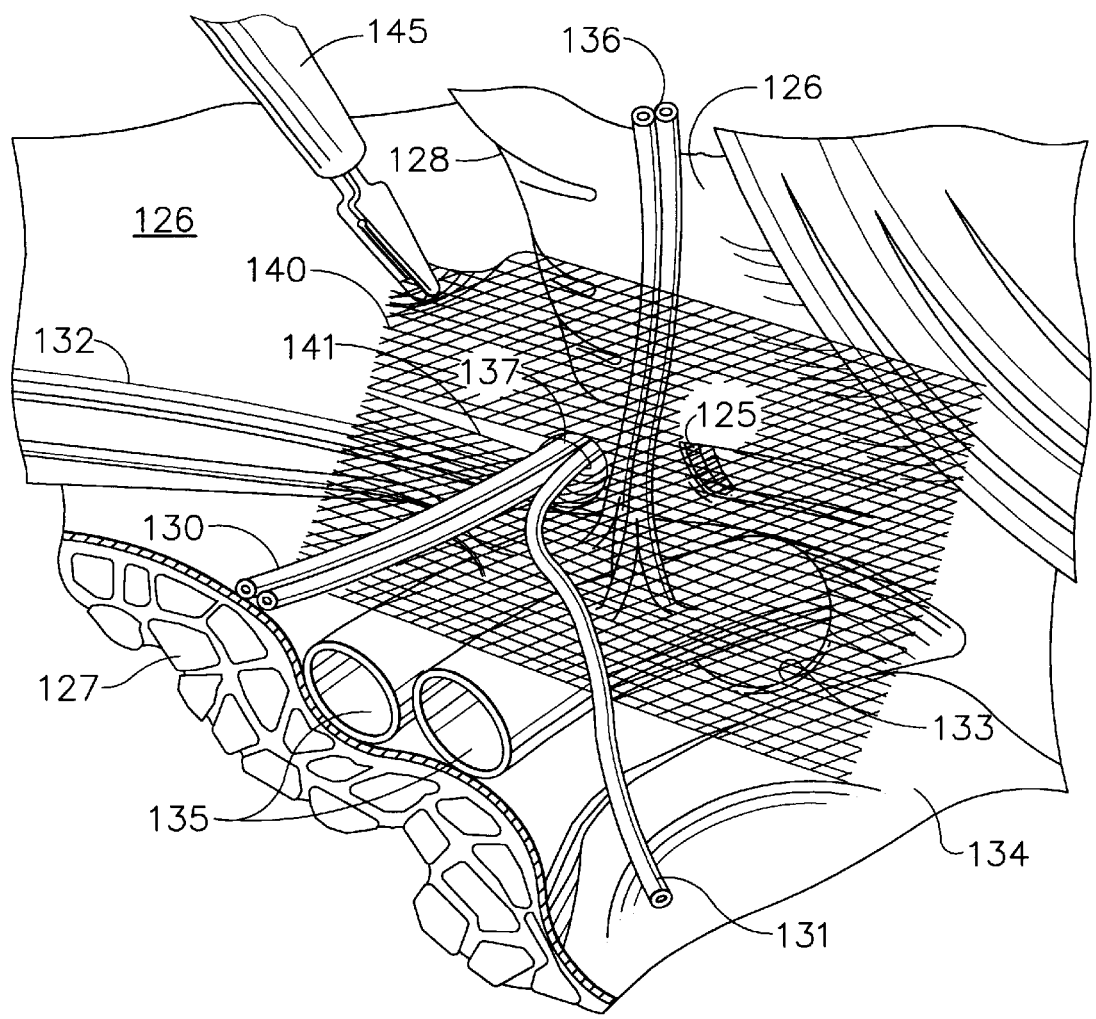
FIG. 16 is a fragmentary perspective view of a surgical grasper instrument placing a mesh patch over a defect or hernia in the inguinal floor of the lower abdomen, particularly the left inguinal anatomy.

Referring now to FIG. 16, one typical application of the surgical instrument of the present invention may be a repair of a defect, such as an inguinal hernia 125, located in inguinal tissue such as the inguinal floor 126. The anatomical structures of the left inguinal anatomy of a human patient are illustrated in order to point out the usefulness of the present invention.

Generally, the inguinal hernia 125 may be accessible through iliacus muscle 127. As can be well appreciated, a network of vessels and nerves exist in the area of a typical inguinal hernia 125, which requires a surgeon to conduct a hernia repair with great skill and caution. For instance, in the transverse abdominis aponeurosis 128, an internal ring 129 permits gastric vessels 130 and Vas deferens 131 to extend therethrough over an edge of inguinal ligament 132. Femoral canal 133 is located near Cooper's ligament 134 and contains external iliac vessels 135 and inferior epigastric vessels 136.

In many cases, the edge of the inguinal ligament 132 and Cooper's ligament 134 serve as anatomical landmarks and support structures for supporting surgical fasteners such as those mentioned previously. The area containing the external iliac vessels 135 and the Vas deferens 131 may be commonly known as "the Triangle of Doom" to surgeons. Accordingly, the surgeon should avoid injuring any of these vessels described above and care must be taken when performing dissection, suturing or fastening within this area.

Figure 17:
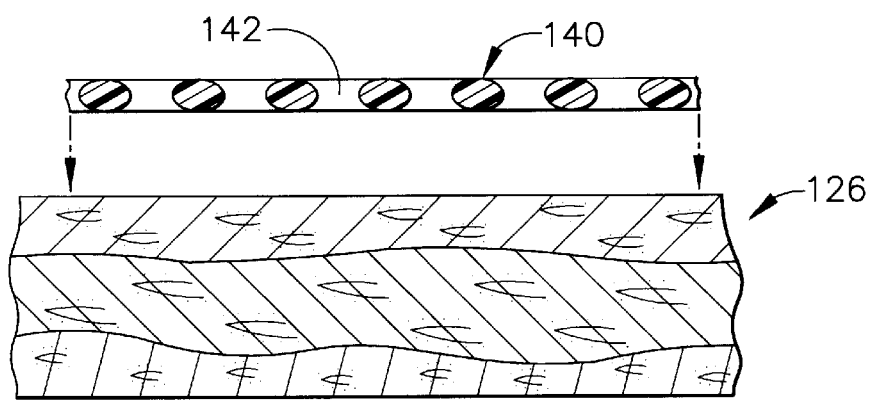
FIG. 17 is a cross-sectional side view of the inguinal floor of the lower abdomen of FIG. 16 illustrating the placement of the mesh patch above the tissue in preparation for repair of the defect according to the present invention.

In FIGS. 16 and 17, a prosthetic or a mesh patch 140 may be placed over the inguinal hernia 125 with a surgical grasping instrument 145 as the first step in the repair of the inguinal hernia 125. The mesh patch 140 may consist of any desired configuration, structure or material. However, the mesh patch 140 may be preferably made of PROLENE™ (a known polymer made up of fibers) and preferably configured as mesh. It may be within the training and comfort zone for surgeons to use the PROLENE™ mesh patch 140 since the mesh patch 140 may be easily sized, such as providing a side slot 141, for accommodating the gastric vessels 130 and the Vas deferens 131.

As illustrated, the mesh patch 140 may be placeable over the inguinal hernia 125 for providing a sufficient barrier to internal viscera (not shown) of the abdomen which would otherwise have a tendency to protrude through the inguinal hernia 125 and cause the patient a great deal of pain and discomfort. FIG. 17 shows a side view of the mesh patch 140 being placed onto the inguinal floor 126. The mesh patch 140 may be now attachable to the inguinal floor 126.

The Method

FIGS. 18–23 are also used to illustrate the method of use of the surgical instrument 35. These cross-sectional side views of the distal end of the shaft 92 show the steps involved in using the surgical instrument 35 as it places a novel fastener 105 of the present invention into the inguinal floor 126 to attach the mesh patch 140 thereto.

Figure 18:
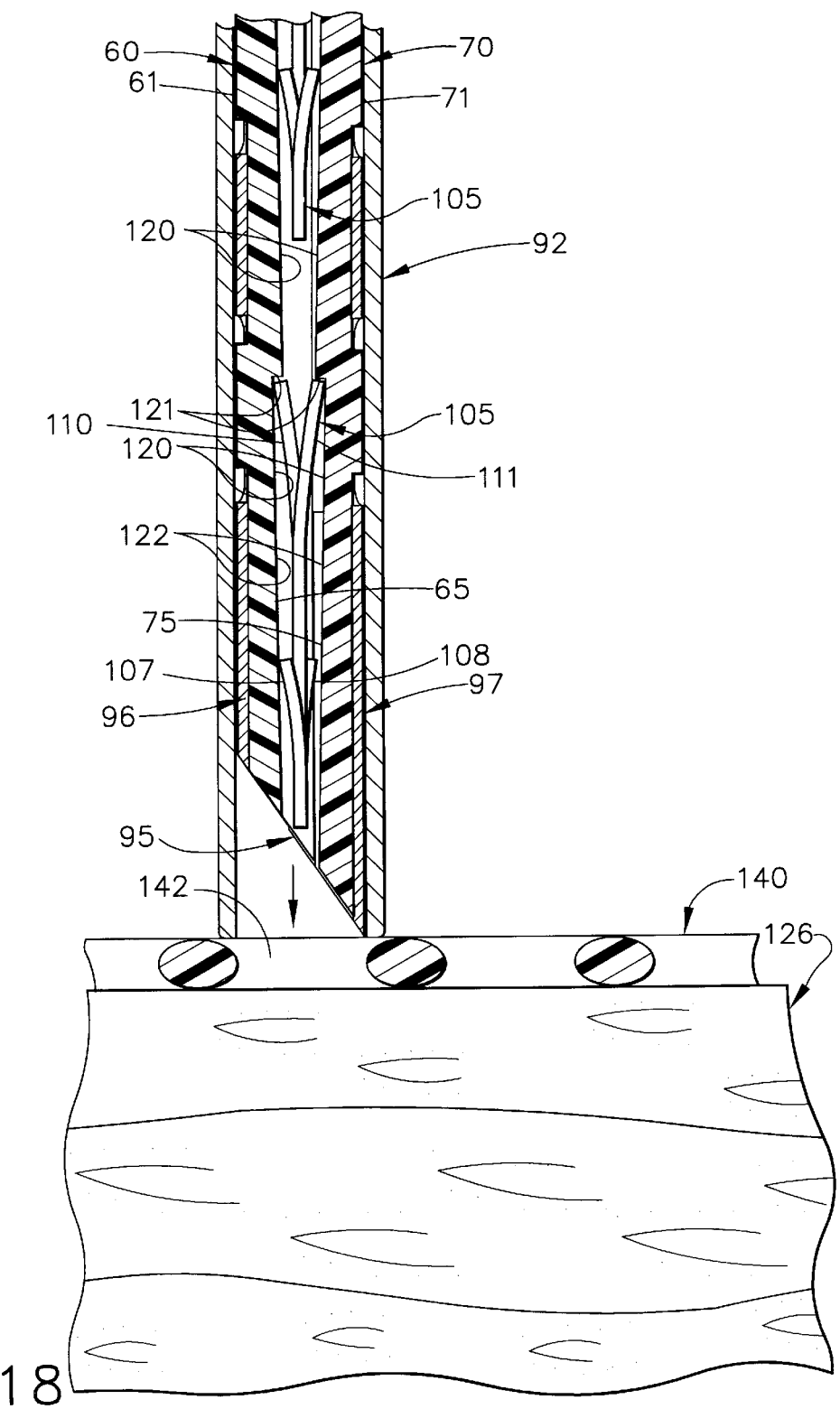
FIG. 18 is a cross-sectional side view of the inguinal floor of the lower abdomen wherein the distal end of the shaft of FIG. 14 is pushing the mesh patch downward onto the inguinal floor, and the end effector is moving downwardly within the shaft with a fastener contained therein.
Figure 19:
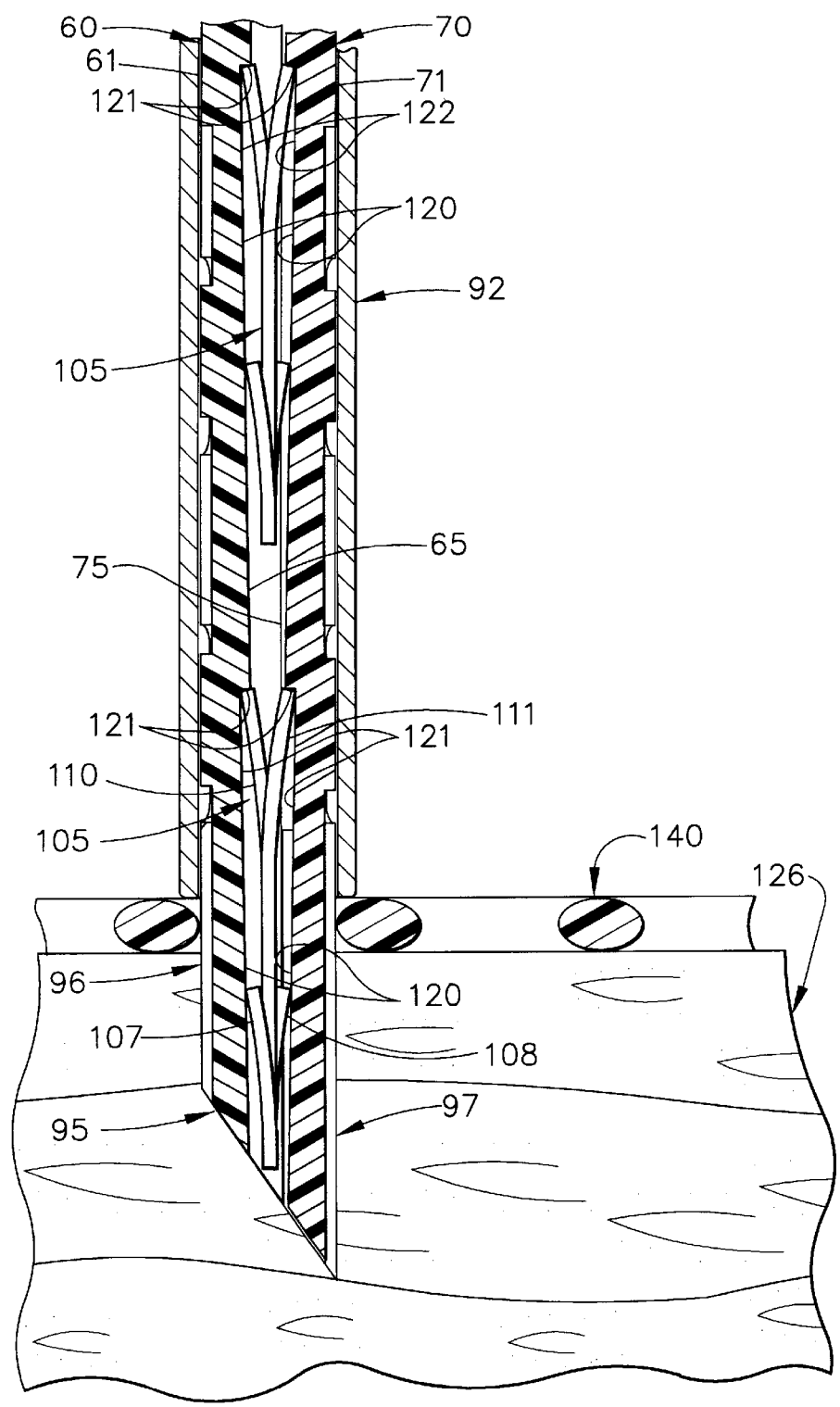
FIG. 19 is a cross-sectional side view of the inguinal floor and instrument of FIG. 18 wherein the end effector of the present invention is extended from the shaft and into the inguinal floor, the end effector containing a fastener of the preferred invention therein.

FIG. 18 is a cross-sectional side view of the inguinal floor 126 of the lower abdomen wherein the surgeon has placed the distal end of the shaft 92 into the area near the patient's inguinal hernia 125. The surgeon has selected an attachment point or surgical site and is using the distal end of the surgical instrument 35 to push the mesh patch 140 downward onto the inguinal floor 126. The distal end of the shaft 92 may be deliberately positioned over an opening 142 within the mesh patch 140 for the placement of a fastener 105 therethrough. The position of the end effector 95 within the cross-sectioned shaft 92 indicates that the trigger 85 has been partially activated by the surgeon. The partial movement or activation of the trigger 85 can translate or move the first and second sliders 60, 70 distally (downwardly in FIG. 14) from the initial position shown in FIG. 14.

As illustrated in FIG. 19, the surgeon has continued to actuate or move the trigger 85, to the first position (FIGS. 2, 5, and 6), and has fully extended or translated the first and second sliders 60, 70 of the end effector 95 from the shaft 92. The extended end effector 95 has penetrated through the opening 142 within the mesh patch 140 and into the inguinal floor 126. Although shielded from tissue contact by the end effector 95, the first and second barbs 107, 108 of the distal most fastener 105 are placed within tissue of the inguinal floor 126.

Continued actuation of the trigger 85 by the surgeon moves the trigger 85 from the from the first partially closed position shown in FIGS. 5 and 6 to the second fully closed position shown in FIGS. 7 and 8. In this position, the indexing mechanism of the surgical instrument 35 may be actuated and an automatic sequence of actions occurs beginning with the reciprocation or movement of the first slider 60 proximally as indicated by the arrow in FIG. 20.

In FIG. 20, the first slider 60 has partially moved or retracted into the shaft 92. This action can released the first and second barbs 107, 108 of the distal most fastener 105 from the constrained condition shown in FIG. 19 and fixably engaged the first barb 107 with the tissue of the inguinal floor 126. The barbs 107, 108 of the distal fastener 105, when released, can snap open to the positions shown in FIG. 20, bending the distal most fastener 105.

Once actuated, the first slider 60 can continue to move distally into the surgical instrument 35 until it returns to the to the initial start position within the shaft 92 as shown in FIG. 21. When the first slider 60 is at this position, the second slider 70 may be automatically released to move or reciprocate distally into the shaft 92 as indicated by the arrow.

As shown in FIG. 21, the first slider 60 is the initial start position of FIG. 15, and can fully release the distal fastener 105. The second barb 108 and second leg 111 may bias the distal fastener 105 into the portion of the shaft 92 previously occupied by the first feed member 61 of the first slider 60. This bias can further engage the first barb 107 of the distal fastener 105 with the inguinal floor 126.

In FIG. 22, the second slider 70 has automatically retracted distally into the shaft 92 to the first start position and can fully release the second barb 108 of the distal fastener 105 to engage with the tissue of the inguinal floor 126. The second leg 111 of the distal fastener 105 can be released from the second slider 70 and both the first and the second legs 110, 111 can expand outwardly within the shaft 92.

Figure 23:
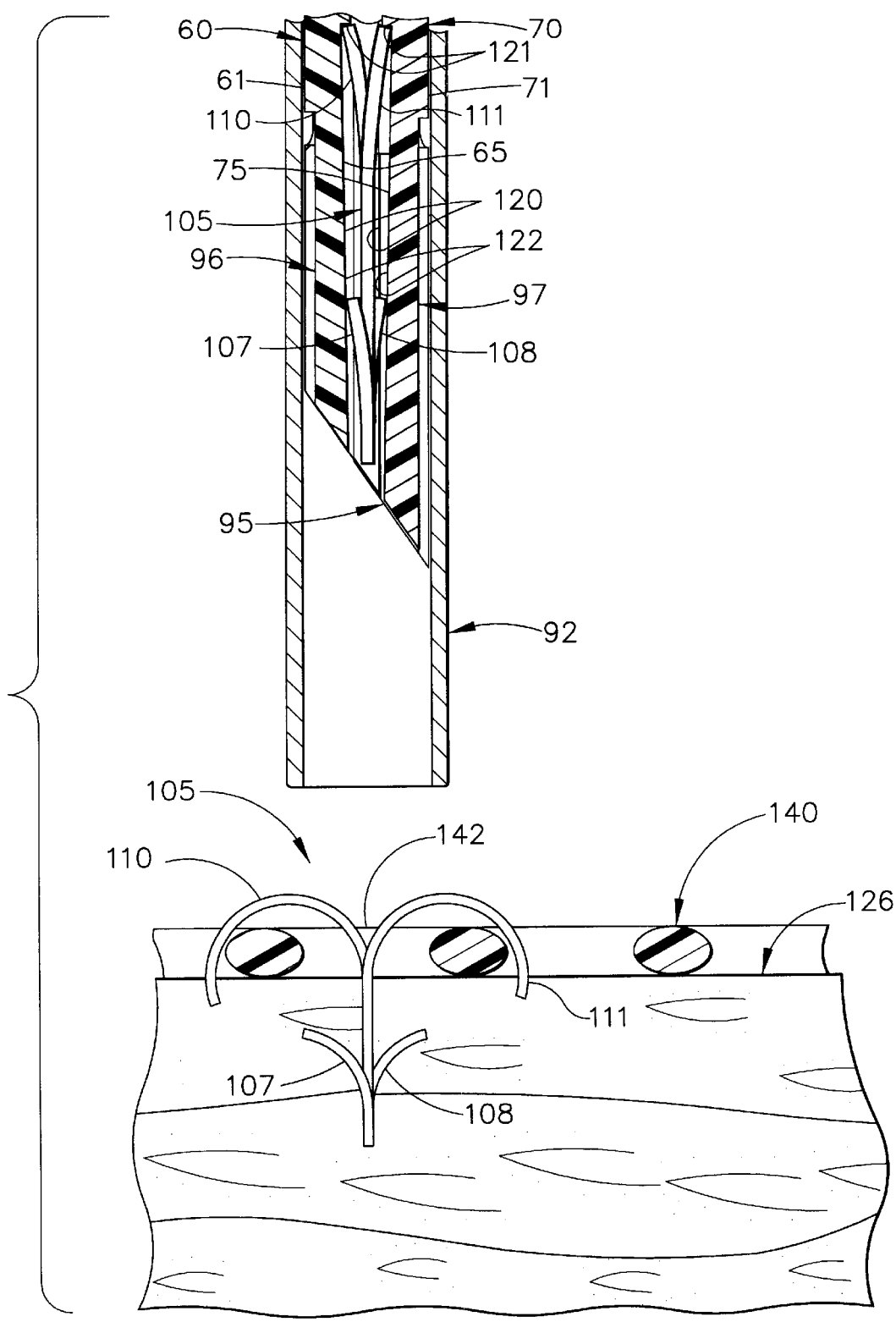
FIG. 23 is a cross sectional side view of FIG. 22 wherein the shaft of the surgical instrument of FIG. 22 has moved upwardly to release the arms of the fastener of the present invention, the released arms attaching the surgical mesh to the inguinal floor.

Finally, the surgeon can release the trigger 85 which returns to the initial open position of FIG. 1 and withdraws the distal end of the shaft 92 away from the mesh patch 140, and from the distal fastener 105 that may be engaged or attached to the inguinal floor 126. As shown in FIG. 23, the first and second barbs 107, 108 of the fastener 105 of the present invention are firmly planted within the inguinal floor 126 and the first and second legs 110, 111 may when released from the shaft 92, snap back to their original everted shape (FIGS. 9 and 10). The mesh patch 140 may be fixedly held against the inguinal floor 126 by the first and second legs 110, 111 of the fastener 105. The surgical instrument is now ready to attach the mesh patch 140 at another site. To accomplish this, the surgeon merely repositions the distal end of the shaft 92 at another surgical site and actuates the trigger 85 to place or attach another fastener 105 into the inguinal floor 126. This process may be continued until the mesh patch 140 is satisfactorily attached to the inguinal floor 126.

FIGS. 34–37 illustrate the method of use of the alternate surgical instrument 235 as it attaches a mesh patch 140 to the inguinal floor 126 with a fastener 105. Unlike the previously described surgical instrument 35 with two moving sliders 60, 70, alternate surgical instrument 235 can have one moving slider 260 and one fixed slider 270 and may use a different sequencing or movement method to place the fastener 105 into tissue. The previously described sliders 60, 70 can have internal fastener channels 65, 75 (FIG. 2B) to propel the fasteners 105 through the surgical instrument 35. The moving and fixed sliders 260,270 can use the same principle and may have a moving channel 265 in the moving slider 260 and a fixed channel 275 in the fixed slider 270. Like the previously described channels 65,75, the moving and fixed channels 265, 275 can also have sawteeth 120 with steps 121 and inclines 122. The longitudinal distance between the steps 121 can be halved in the alternate surgical instrument 235 while the length of the reciprocation stroke can remain generally the same as the stroke in the surgical instrument 35. Thus, the fastener 105 may be generally moved distally the same distance in either surgical instrument 35, 235. However, in the alternate surgical instrument 235, the second leg 111 of the fastener 105 may be moved distally two sawteeth as the shown by the distal most fastener 105 as it moves from the position of FIG. 34 to the position of FIG. 35.

Figure 34:
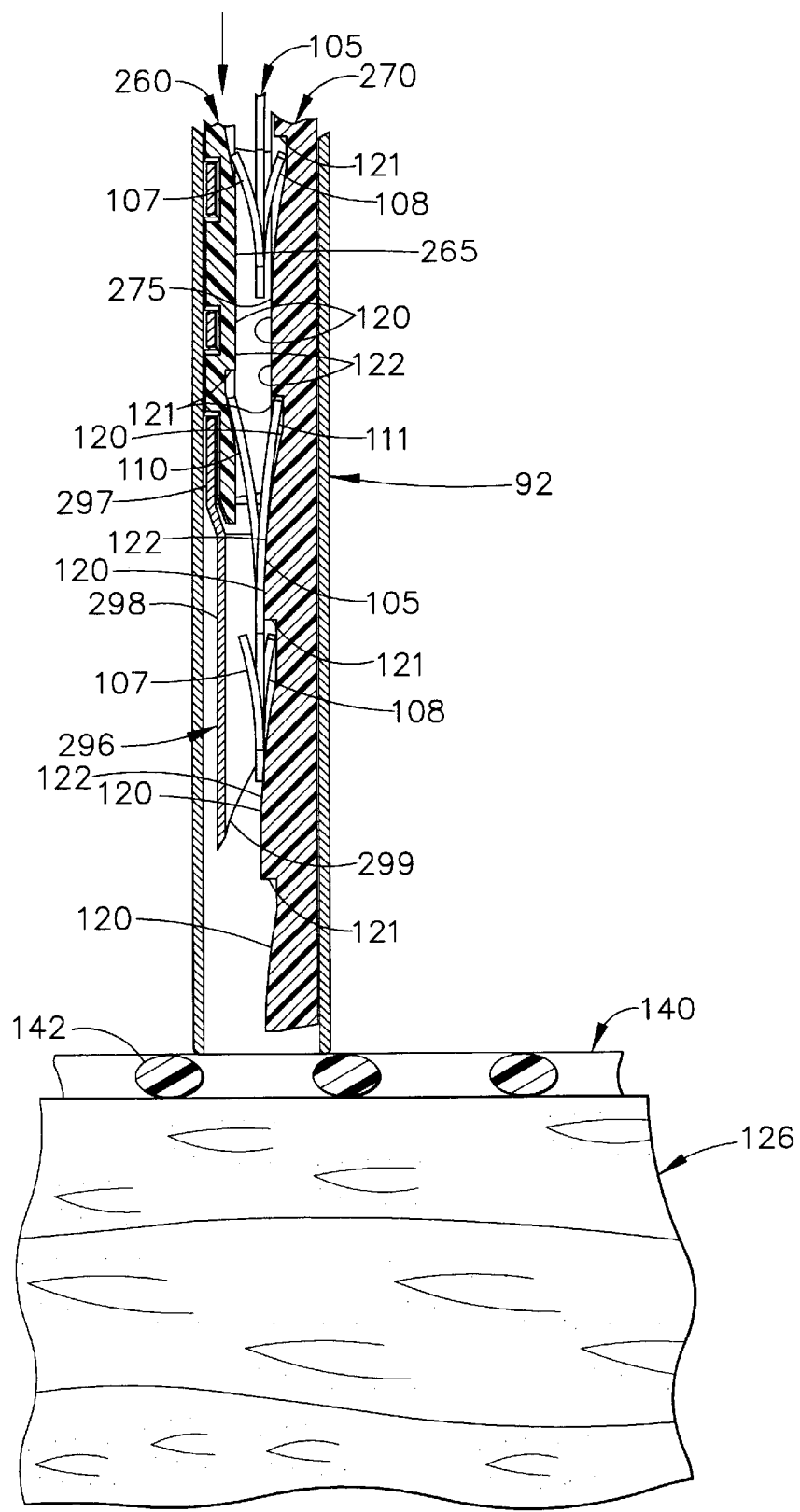
FIG. 34 is a cross-sectional side view of a distal end of a shaft of the alternate surgical instrument wherein the shaft is pushing a hernia mesh against tissue and showing the positions of the moving and fixed sliders therein with a plurality of surgical fasteners contained therebetween.
Figure 35:
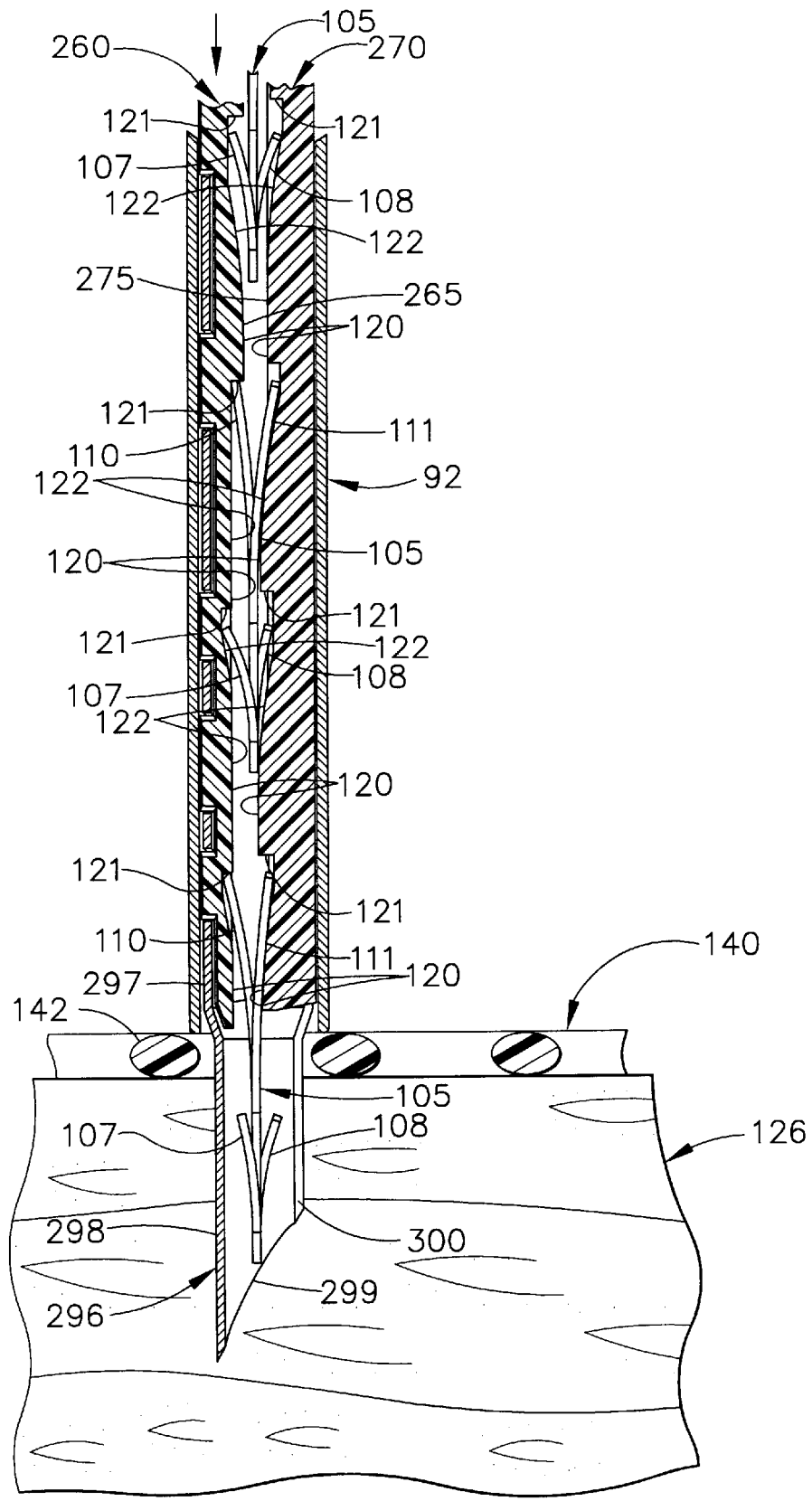
FIG. 35 is a cross-sectional side view of the inguinal floor and shaft of FIG. 34 wherein the moving slider and an attached end effector of the alternate invention is extended from the shaft and into the hernia mesh and inguinal floor, the end effector containing a fastener of the preferred invention therein.

FIG. 34 shows a cross-sectional side view of the inguinal floor 126 of the lower abdomen wherein the surgeon can use a distal end of the shaft 92 of the alternate surgical instrument 235 to push a mesh patch 140 downwardly against the inguinal floor 126. The distal end of the shaft 92 may be deliberately positioned over an opening 142 within the mesh patch 140 for the placement of a fastener 105 therethrough. The alternate trigger 285 is in the first open position (FIG. 31) and the moving slider 260 can be in the proximal most position. The fixed slider 270 is fixed relative to the shaft 92, and the moving slider 260 may be poised to propel the fasteners 105 distally and the distal most fastener 105 (shown on bottom) into tissue. The second legs 111 of the fasteners 105 can be in contact with a step 121 of the fixed slider 270. As shown, a small amount of distal (downward) motion of the moving slider 260 may bring a step 121 of the moving slider 260 into contact with the first leg 110 of the fasteners 105. A moving stab plate 296 may be fixedly attached to the moving slider 260 and is best shown in FIG. 35. Moving stab plate 296 may be a stepped cylinder having two different diameter sections, a large diameter proximal section 297 and may be fixedly attached to the moving slider 260 with a small diameter distal section 298 extending distally therefrom. Distal section 298 has a piercing point 299 at a distal end that can penetrate tissue. A slot 300 can extend longitudinally through proximal section 297 and distal section 298 to provide clearance around a proximal end of the fixed slider 270. The distal most fastener 105 may be located within the moving stab plate 296 with the first barb 107 in contact with an inner surface of the distal section 298 and the second barb 108 in contact with the fixed slider 270. The distal most portion of the fixed slider 270 may be located within the slot 300.

FIG. 35 shows the effects of moving the alternate trigger 285 from the first open position to the second closed position. An arrow is provided to show the direction of motion. This action can move the moving slider 260 and the fasteners 105 distally to the distal most position. The moving stab plate 296 may pierce the mesh patch 140 and the inguinal floor 126 to place the distal section 298 of the moving stab plate 296 into tissue. The barbs 107,108 can be constrained from outward movement by contact with the inner surface of the distal section 298. The first leg 110 of the fastener 105 may be operatively engaged with the distal most step 121 of the moving slider 260 to hold distal most fastener 105 in the position shown.

Figure 36:
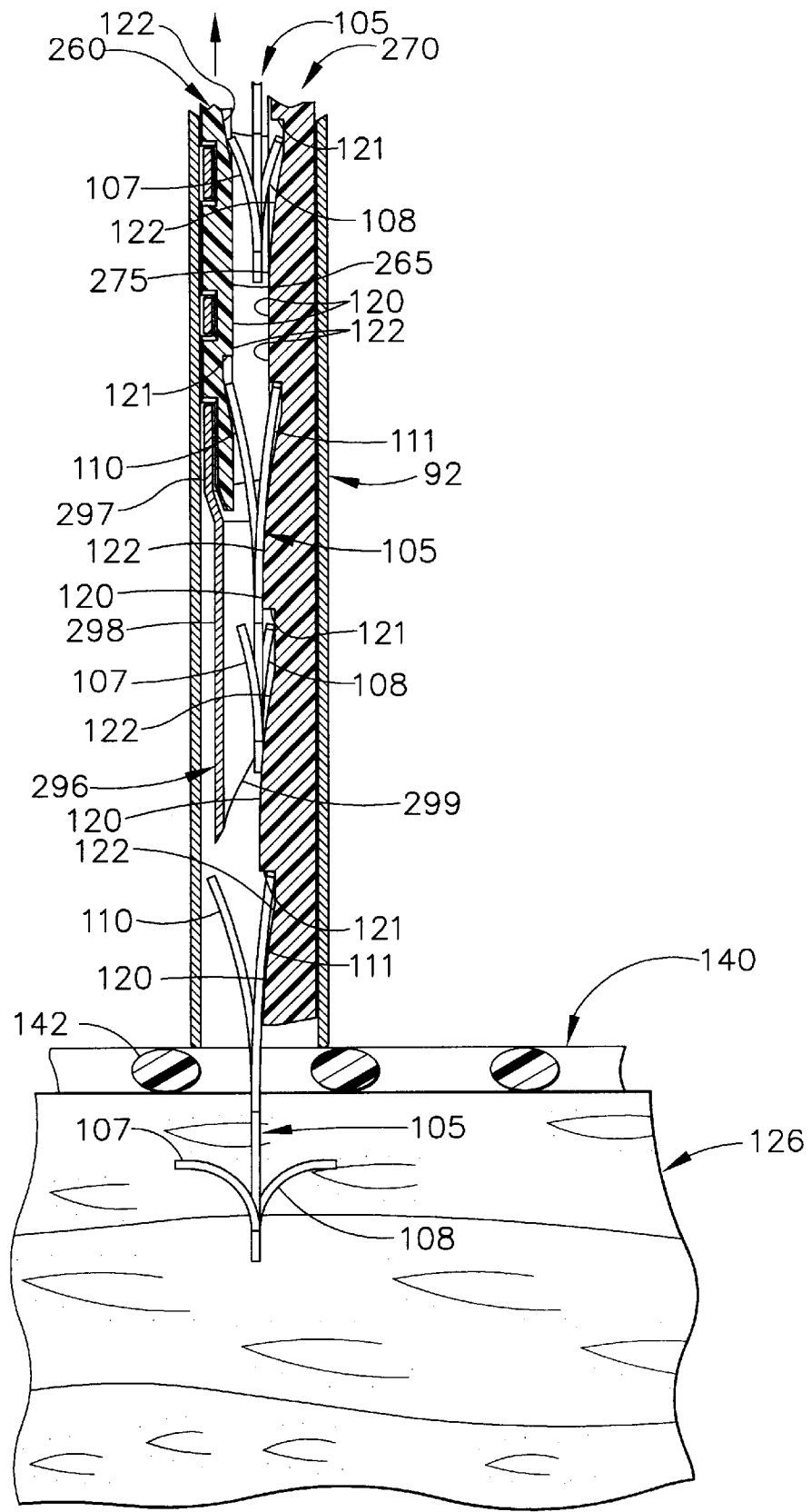
FIG. 36 is the cross-sectional side view the inguinal floor and shaft of FIG. 35 wherein the slider and attached end effector of the alternate surgical instrument is fully retracted into the shaft, the full retraction releasing barbs of the fastener into the tissue of the inguinal floor.
Figure 37:
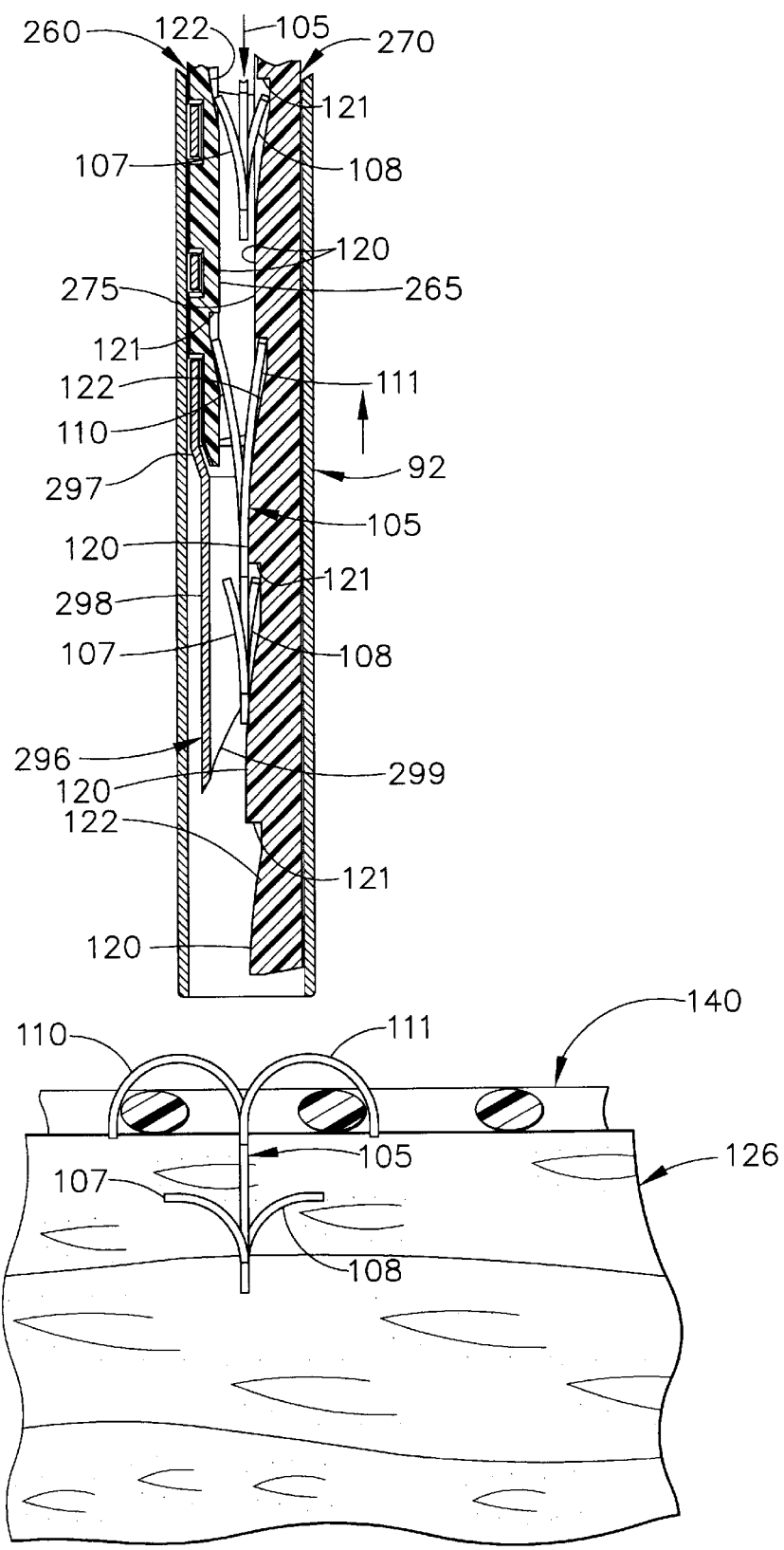
FIG. 37 is a cross sectional side view of FIG. 36 wherein the shaft of the alternate surgical instrument has moved upwardly to release a pair of legs of the fastener from the shaft, the released legs attaching the surgical mesh to the inguinal floor.

In FIG. 36, the alternate trigger 285 of the alternate surgical instrument 285 has been released and the moving slider 260 has returned proximally (see arrow) to the proximal most position (FIGS. 34, 37). As the moving slider 260 began to move proximally from the position shown in FIG. 35, the moving slider 260 can move the fasteners 105 proximally a slight amount. This proximal motion may bring an end of each of the second legs 111 of the fasteners 105 into contact with a respective step 121 of the fixed slider 270 and can prevent additional proximal motion of the fasteners 105. The proximal motion of the moving stab plate 296 back into the shaft 92 can release the first and second barbs 107, 108 of the distal most fastener 105 from contact with the fixed slider 270. Upon release, the first and second barbs 107, 108 may fully deploy to the position shown to retain the distal most fastener 105 in tissue. The first and second legs 110,111 of the distal most fastener 105 may be held in the constrained position shown between the shaft 92 and the distal most sawtooth 120 of the fixed slider 270.

In FIG. 37, the surgeon is moving the surgical instrument proximally (see arrow) away from the mesh patch 140 and inguinal floor 126. The distal most fastener may be retained within the inguinal floor by the barbs 107,108 and the proximal motion of the alternate surgical instrument 235 can withdraw the first and second legs 110,111 of the distal most fastener from the shaft 92. When released, the first and second legs 110,111 of the fastener 105 can snap back to the original everted shape (FIGS. 9 and 10) to secure the mesh patch 140 to the inguinal floor. As shown, the mesh patch 140 may be fixedly held against the inguinal floor 126 by the first and second legs 110, 111 of the fastener 105. The alternate surgical instrument 235 can now ready to attach the mesh patch 140 at another site. To accomplish this, the surgeon merely repositions the distal end of the shaft 92 at another surgical site and actuates the alternate trigger 285 to place or attach another fastener 105 into the inguinal floor 126. This process is continued until the mesh patch 140 may be satisfactorily attached to the inguinal floor 126

The Lockout Mechanism

The surgical instrument 35 of the present invention (FIG. 1) contains a plurality of fasteners 105. As the surgeon repeatedly fires the instrument during the attachment of the prosthetic, the number of fasteners 105 stored therein steadily decreases. When the final fastener 105 is placed into tissue, the surgeon has no way of knowing when the instrument is emptied of fasteners 105 and can attempt to fire the empty surgical instrument 35 on tissue. A lockout mechanism may be provided within the surgical instrument 35 to lock the trigger 85 when the surgical instrument 35 is empty.

As described previously, the trigger 85 can have a lockout arm 88 fixably attached to and extending therefrom. Actuation of the trigger 85 may move the lockout arm 88 from the initial position of FIG. 3 to a first partially closed position within the handle 40, and into contact with the lockout wheel 100 rotatably mounted within the wheel receptacle 48 as shown in FIG. 24.

Figure 24:
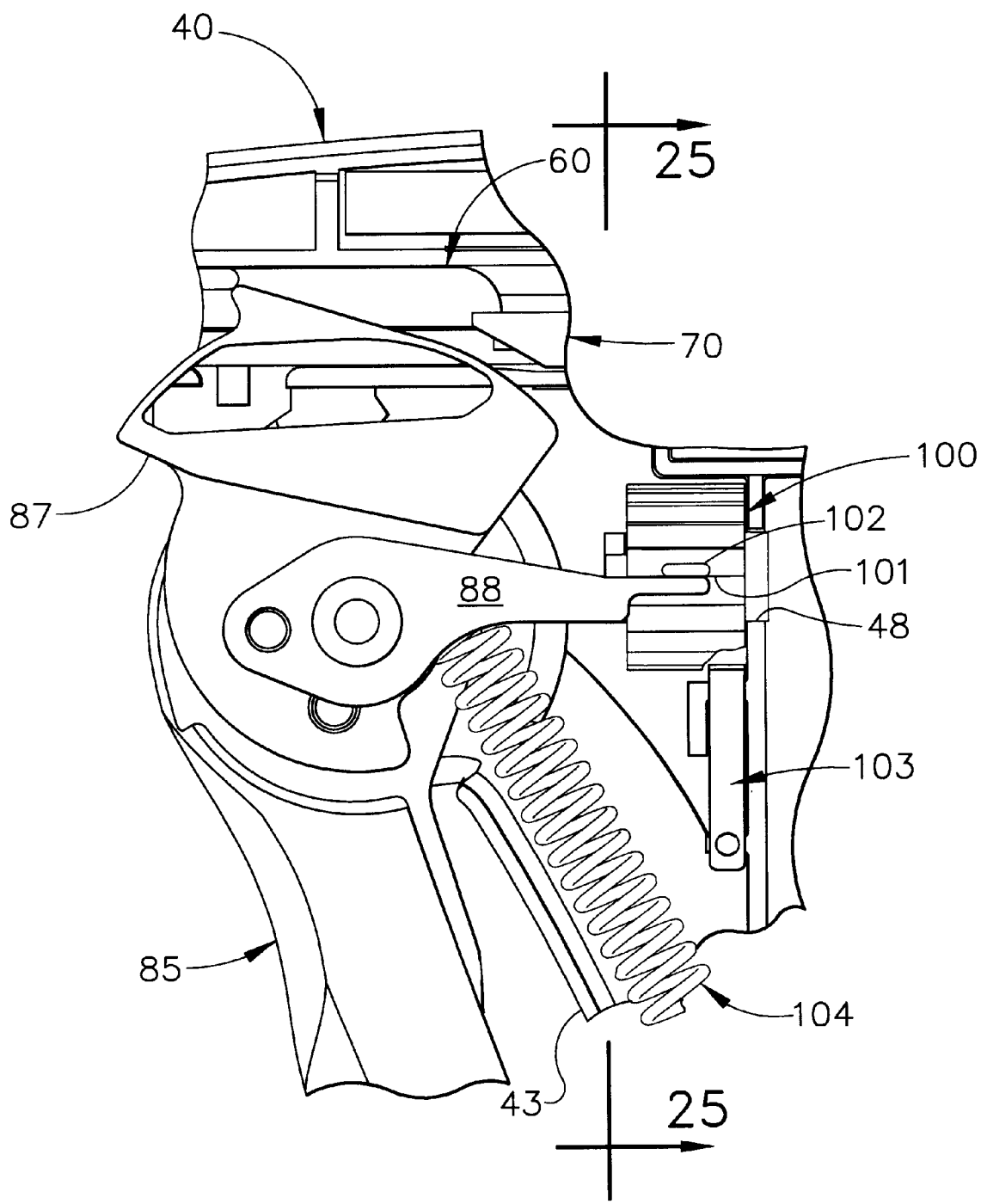
FIG. 24 is a is a fragmentary side-view of a trigger lockout mechanism of the present invention of FIG. 1 with a lockout arm fixably attached to the pivotable trigger, and operably coupled with a lockout wheel.

In FIG. 24, the trigger 85 has rotated lockout arm 88 counter-clockwise to engage with a tooth 101 of the lockout wheel 100. A lockout tab 102 can be located just above the lockout arm 88 and extends outwardly from the lockout wheel 100. A lockout detent 103 can be attached to and extends outwardly from the right handle half 41 towards the viewer to operably engage with the lockout wheel 100. A small cutout can be provided within the lower portion of the lockout wheel 100 to show the outwardly extending end of the lockout detent 103.

FIG. 25 is a distal view taken across cross-section 25—25 in FIG. 24, and shows the necessary portions of the key elements so that the reader can understand the operation of the lockout mechanism. The lockout mechanism of the present invention may comprise the lockout wheel 100, the lockout detent 103 and the lockout arm 88 extending from the trigger 85. Lockout wheel 100 is shown perpendicular to the axis of rotation and can have lockout detent 103 operably engaged with a lockout tooth 101 to prevent clockwise rotation of the lockout wheel 100. The lockout arm is cross-sectioned by the cutting plane 25—25 and two cross-sections are taken across the lockout arm 88. A first section 88a can be taken across the distal end of the lockout arm 88 when the lockout arm is in the initial position, a second section 88b can be taken across the lockout arm 88 to show the actual position of the lockout arm 88. An arrow is provided to identify the direction of motion of the second section 88b of the lockout arm 88.

The lockout wheel 100 of the present invention can have the same number of teeth 101 around its circumference as the surgical instrument 35 has fasteners 105. When the trigger 85 is fully actuated to place a fastener 105 into tissue, the lockout arm 88 can be brought into contact with the lockout wheel 100 to rotate or index the lockout wheel 100 counter-clockwise one tooth 101 as shown in FIG. 26. When the trigger 85 is released after the actuation, the lockout detent 103 can prevent the lockout wheel 100 from rotating clockwise as the lockout arm 88 returns to the initial position 88a. Thus, one full actuation of the trigger 85 can rotate the locking wheel 100 one tooth 101, and firing all of the fasteners 105 can rotate the lockout wheel 100 one full revolution.

FIGS. 27–29 show how the lockout tab 102 can operatively lock the lockout arm 88 (and the trigger 85) in the fully actuated or closed position as the last fastener 105 can be fired. In FIG. 27, the lockout wheel has rotated nearly one full revolution from the first position of FIG. 25. This is indicated by the new position of the lockout tab 102. The second section 88b of the lockout arm 88 is shown moving upwardly, has just cleared the lockout tab 102, and can be contacting the final lockout tooth 101. In FIG. 28, the second section 88b of the lockout arm 88 can be shown in the fully actuated or closed position and the lockout tab 102 can rotate in under the second section 88b of the lockout arm 88. When the trigger 85 is released, the second section 88b of the lockout arm 88 can move downwardly to contact the lockout tab 102 and can rotate the lockout wheel 100 clockwise to engage tooth 101 with the lockout detent 103 (FIG. 29). The engagement with the lockout detent 103 can prevent the lockout wheel 100 from rotating clockwise and can lock the second section 88*b* of the lockout arm 88. Thus, in FIG. 29, the second section 88*b* of the lockout arm 88 (and trigger 85) may be locked in the first partially closed position by the lockout detent 103 which prevents the trigger 85 of the surgical instrument 35 from opening.

FIGS. 31–33 show an alternate lockout mechanism and the movement of the elements of the lockout mechanism as the alternate trigger 285 may be fired or reciprocated from the first open position (FIG. 31) to the second closed position (FIG. 32) and back to the first open position (FIG. 33). The alternate lockout mechanism provides many of the same features of the previously described lockout mechanism such as a rotating lockout wheel, but can offer an alternate lockout that locks the alternate trigger 285 in the open position. The alternate lockout mechanism can have a disk-like alternate lockout wheel 205 that mounts in alternate handle 240 and rotates in a counterclockwise direction. The alternate lockout wheel 205 can comprise a disk face 206 and a plurality of angled counter teeth 207 that extend therefrom. If desired, the lockout mechanism can have one angled counter tooth 207 for each fastener 105 stored within the alternate surgical instrument 235. A counter slot 207 can also be located in the disk face 206 of the alternate lockout wheel 205. A one way detent arm 209 (FIG. 33) can be located on the backside of the alternate lockout wheel 205 to prevent clockwise rotation of the alternate lockout wheel 205. A first marker 206*a* and a second marker 206*b* may be located on the disk face 206 at specific angular locations, the purpose of which will become apparent in the assembly description below.

Alternate trigger 285, (FIGS. 30–33) can be pivotally mounted within the alternate handle 240, and can have an alternate counter arm 288 extending proximally therefrom. Alternate counter arm 288 can have a proximal end 289 that can operably engage with the alternate lockout wheel 205. A lock post 290 can extend from a backside of the alternate trigger 285 (FIG. 33).

A locking member 210 can comprise an elongated member having a retainer 211 at a proximal end, a locking tab 212 extending downwardly from the locking member 210, and a locking bore 213 adjacent to a distal end (FIG. 33). The locking member 210 can be a spring so that it can deflect during operation.

The lockout mechanism can be assembled by first capturing the retainer 211 of the locking member 210 in the right alternate handle half 241. Locking member 210 can become a spring cantilever beam extending distally from the capture point. Next, the alternate lockout wheel 205 can be placed onto a post (not shown) extending from the right alternate handle half 241. This placement brings the one way detent arm 209 (FIG. 33) into contact with one of a plurality of detent teeth 248 extending from the right alternate handle half 241 (FIG. 30). The alternate lockout wheel 205 is shown oriented with the first marker 206*b* aligned with the locking tab 212 of the locking member 210. This alignment position can be used when the alternate surgical instrument holds ten fasteners 105 and can provide ten firings before the lockout may be activated. When the alternate surgical instrument 235 holds twenty fasteners, the alternate lockout wheel 205 can be oriented with the second marker 206*a* to provide twenty firings before the lockout may be activated.

Lastly, the alternate trigger 285 can be placed into the right alternate handle half 241, trigger spring 104 can be connected to the alternate trigger 285 and the right handle half 241 and the left alternate handle half 242 can be attached to secure the alternate locking mechanism and other components. Attachment of the left alternate handle half 242 may push a backside of the disk face 206 of alternate locking wheel 205 into contact with the locking tab 212 of the locking member 210 to deflect a distal end of the locking member 210 inwardly from the contact. This deflection can be best seen in FIG. 33 as the gap between the lock post 290 and the locking member 210.

The alternate lockout mechanism can operate as follows. As the alternate trigger 285 is moved from the first open position of FIG. 31 to the second closed position of FIG. 32, the proximal end 289 of the alternate counter arm 288 can deflect up and over the a stationary counter tooth 208*a*. The counter tooth 208*a* is shown in FIG. 31 as just above and generally behind the proximal end 289 of the alternate counter arm 288. The alternate lockout wheel 285 may remain stationary during this action as one way detent arm 209 lockingly engages with one of the plurality of detent teeth 248 (FIG. 30) located in the right alternate handle half 241. This locking engagement can prevent clockwise rotation of the alternate locking wheel 285. Additionally, the one way detent arm 209 can provide sliding action during counterclockwise rotation of the alternate lockout wheel 205.

Once the proximal end 289 of the alternate counter arm 288 clears the counter tooth 208*a* on alternate lockout wheel 205, the proximal end 289 can freely move in an arc to the position of FIG. 32. Next, the alternate trigger 285 may be released to return from the second closed position of FIG. 32 back to the first open position of FIGS. 31 & 33. As the alternate trigger 285 approaches the first open position, the proximal end 289 of the alternate counter arm 288 can move back into contact with the previously described counter tooth 208*a* and push tooth 208*a* downwardly to the position shown in FIG. 33. Thus, each firing or reciprocation of the alternate trigger 285 can eject one fastener 105 from the alternate surgical instrument 235 and indexes the alternate lockout wheel 205 one tooth. Continued firing or reciprocation of the alternate trigger 285 can empty the fastener 105 from counter by one tooth for each firing. This process continues until the last fastener 105 may be ejected from the alternate surgical instrument and the counter slot 207 moves counterclockwise from a position such as the 6:00 o'clock position shown in FIGS. 31–32 to a 12:00 o'clock position (not shown). When the counter slot 207 is at the 12:00 o'clock position, the locking tab 212 of the locking member 210 may be released to spring or move into the counter slot 207. This action can move the locking bore 213 of the locking member 210 away from the right alternate handle half 241 and can capture the lock post 290 with the locking bore 213. This action can lock out the alternate trigger 285 in the first open position when the last fastener 105 is fired.

It will be recognized that equivalent structures may be substituted for the structures illustrated and described herein and that the described embodiment of the invention is not the only method or structure which may be employed to implement the claimed invention. As one example of an equivalent method or structure which may be used to implement the present invention, is a feeding mechanism that can distally move a pair of opposed members that move a fastener distally, the distal movement can place the distal end of the fastener into tissue, can partially deploy a distal end of the fastener into tissue by moving one member proximally, and can fully deploy the distal end of the fastener into tissue by moving the remaining member proximally. As a further example of an equivalent method or structure which may be used to implement the present invention, a feeding mechanism can be provided that can consecutively reciprocate a pair of opposed members in opposite directions to propel the fastener distally, can partially place the distal end of the fastener into tissue with a first reciprocation and can fully place the fastener into tissue with a second reciprocation. In addition it should be understood that every structure described above has a function and such structure can be referred to as a means for performing that function.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A method for delivering a plurality of individual surgical fasteners, said method comprising:
   a. providing a surgical fastener delivery device having a drive mechanism with distal and proximal ends, said drive mechanism comprising moving and fixed opposing members, said moving member being moveable proximally and distally with respect to said delivery device, and said fixed member being fixed with respect to said delivery device, said device having the plurality of surgical fasteners located between said moving and said fixed members;
   b. penetrating tissue with said delivery device and placing a distal end one of the surgical fasteners within tissue, by moving said moving member distally; and
   c. deploying a distal end of one of the surgical fasteners by moving said moving member proximally.

2. The method of claim 1 further including the step of deploying the surgical proximal end of said surgical fastener by moving said device proximally.

3. The method of claim 2 further including the step of placing a prosthetic onto said tissue prior to the step of penetrating tissue, wherein said step of penetrating tissue further includes the step of penetrating said prosthetic.

4. A method for repairing a hernia within a patient, said method comprising:
   a. providing a surgical fastener delivery device having a drive mechanism with distal and proximal ends, said drive mechanism comprising a moving and fixed opposing members, said moving member being moveable proximally and distally with respect to said delivery device and said fixed member being fixed relative to said delivery device, said device having a plurality of surgical fasteners located between said first and said second members;
   b. placing a prosthetic over the hernia and tissue adjacent thereto;
   c. penetrating said prosthetic and said adjacent tissue with said deliver device, and placing a distal end one of the surgical fasteners within tissue, by moving said moving member distally; and
   d. deploying a distal end of one of said surgical fasteners into tissue by moving said moving member proximally.

5. The method of claim 4 further including the step of deploying the surgical proximal end of said surgical fastener by moving said device proximally.

6. The method of claim 4 further including delivering additional fasteners by repeating steps b–d at least once.

* * * * *